US012582768B2

(12) United States Patent
Sucheta et al.

(10) Patent No.: US 12,582,768 B2
(45) Date of Patent: Mar. 24, 2026

(54) MEDICAMENT DELIVERY SYSTEM, AND ASSOCIATED METHOD

(71) Applicant: Zoetis Services LLC, Parsippany, NJ (US)

(72) Inventors: Susan Leers Sucheta, Kalamazoo, MI (US); Nicholas Alan Wicks, Kalamazoo, MI (US); Derrick Scott Sjodin, Greenville, SC (US); Christopher Jeremy Block, Laramie, WY (US); Laibin Luo, Ridgefield, CT (US)

(73) Assignee: Zoetis Services LLC, Parsippany, NJ (US)

( * ) Notice: Subject to any disclaimer, the term of this patent is extended or adjusted under 35 U.S.C. 154(b) by 928 days.

(21) Appl. No.: 17/674,415

(22) Filed: Feb. 17, 2022

(65) Prior Publication Data

US 2022/0331516 A1      Oct. 20, 2022

Related U.S. Application Data

(60) Provisional application No. 63/152,096, filed on Feb. 22, 2021.

(51) Int. Cl.
 *A61M 5/142* (2006.01)
(52) U.S. Cl.
 CPC ..... *A61M 5/14276* (2013.01); *A61M 2205/04* (2013.01); *A61M 2210/1433* (2013.01)
(58) Field of Classification Search
 CPC .......... A61M 5/14276; A61M 2205/04; A61M 31/002; A61M 2210/1433; A61D 7/00;
 (Continued)

(56) References Cited

U.S. PATENT DOCUMENTS 4,309,996 A * 1/1982 Theeuwes ............ A61K 9/0004
424/424
11,523,772 B2 12/2022 Jones et al.
(Continued)

FOREIGN PATENT DOCUMENTS

WO      2022178206 A1      8/2022

OTHER PUBLICATIONS

International Preliminary Report on Patentability for International Application No. PCT/US2022/016916, dated Aug. 31, 2023, 12 Pages.

(Continued)

*Primary Examiner* — James D Ponton
(74) *Attorney, Agent, or Firm* — Scott C. Mayhew

(57) ABSTRACT

An intra-orifice medicament delivery system and formation method involve a housing defining an inner chamber extending along a longitudinal axis, with the chamber wall defining one or more openings therethrough. A retention arrangement extends from the housing, and is adapted to removably retain the housing within a bodily orifice defined by an orifice wall. An osmotic delivery device is disposed within the chamber and includes an osmogen portion and medicament-including portion disposed within a semipermeable membrane. The osmogen portion expands and applies pressure to the medicament-including portion in response to absorption of a liquid from within the bodily orifice permeating through the semipermeable membrane. The medicament-including portion is arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice.

35 Claims, 20 Drawing Sheets

(58) Field of Classification Search
CPC ... A61D 1/08; A61F 6/14; A61F 6/142; A61F 6/144
See application file for complete search history.

(56) References Cited

U.S. PATENT DOCUMENTS

| | | | | |
|---|---|---|---|---|
| 2009/0178682 A1* | 7/2009 | Tal | .......................... | A61F 6/20 |
| | | | | 128/831 |
| 2010/0280464 A1* | 11/2010 | De Graaff | .............. | A61P 13/00 |
| | | | | 29/428 |
| 2015/0088090 A1* | 3/2015 | Macy, Jr. | ............... | A61M 1/83 |
| | | | | 604/266 |
| 2015/0335464 A1 | 11/2015 | De Graaff et al. | | |
| 2020/0253506 A1 | 8/2020 | Jones et al. | | |

OTHER PUBLICATIONS

International Search Report and Written Opinion for International Application No. PCT/US2022/016916, dated Jun. 14, 2022, 14 Pages.
Taiwan Search Report for Taiwan Application No. 111105805, dated Mar. 26, 2025, 1 Page.

* cited by examiner

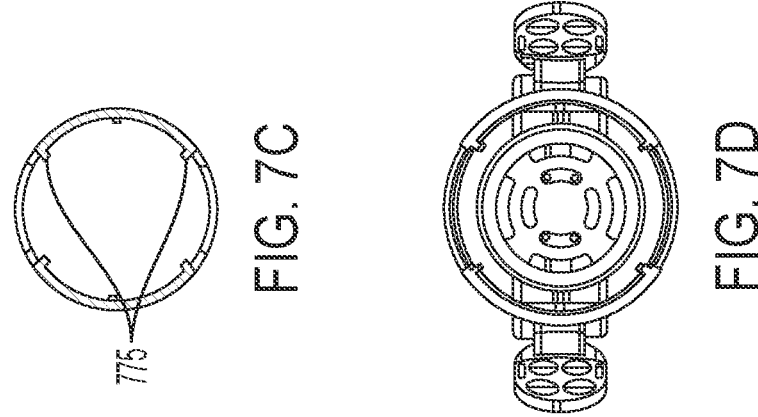
FIG. 7C
FIG. 7D
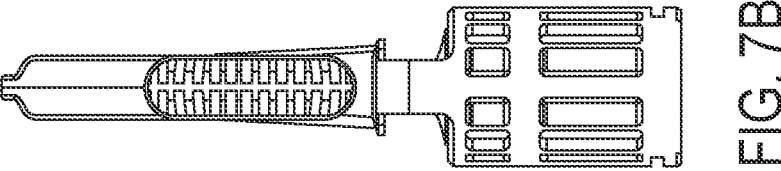
FIG. 7B
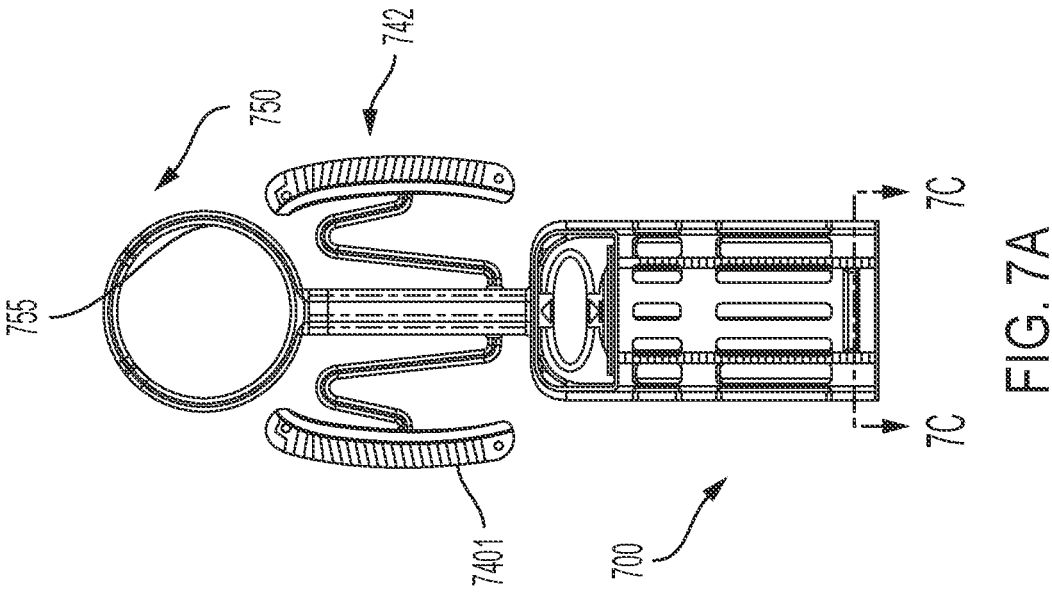
FIG. 7A

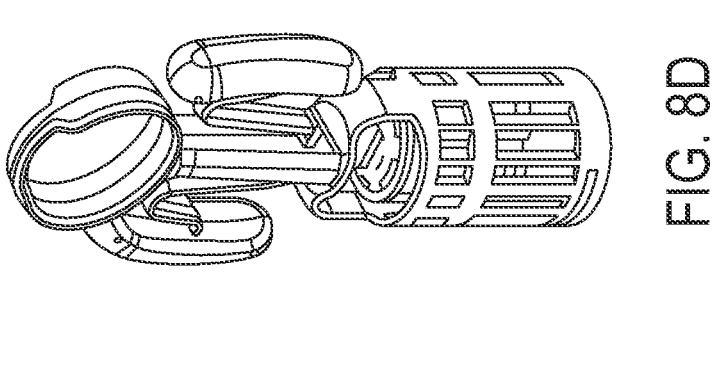
FIG. 8D
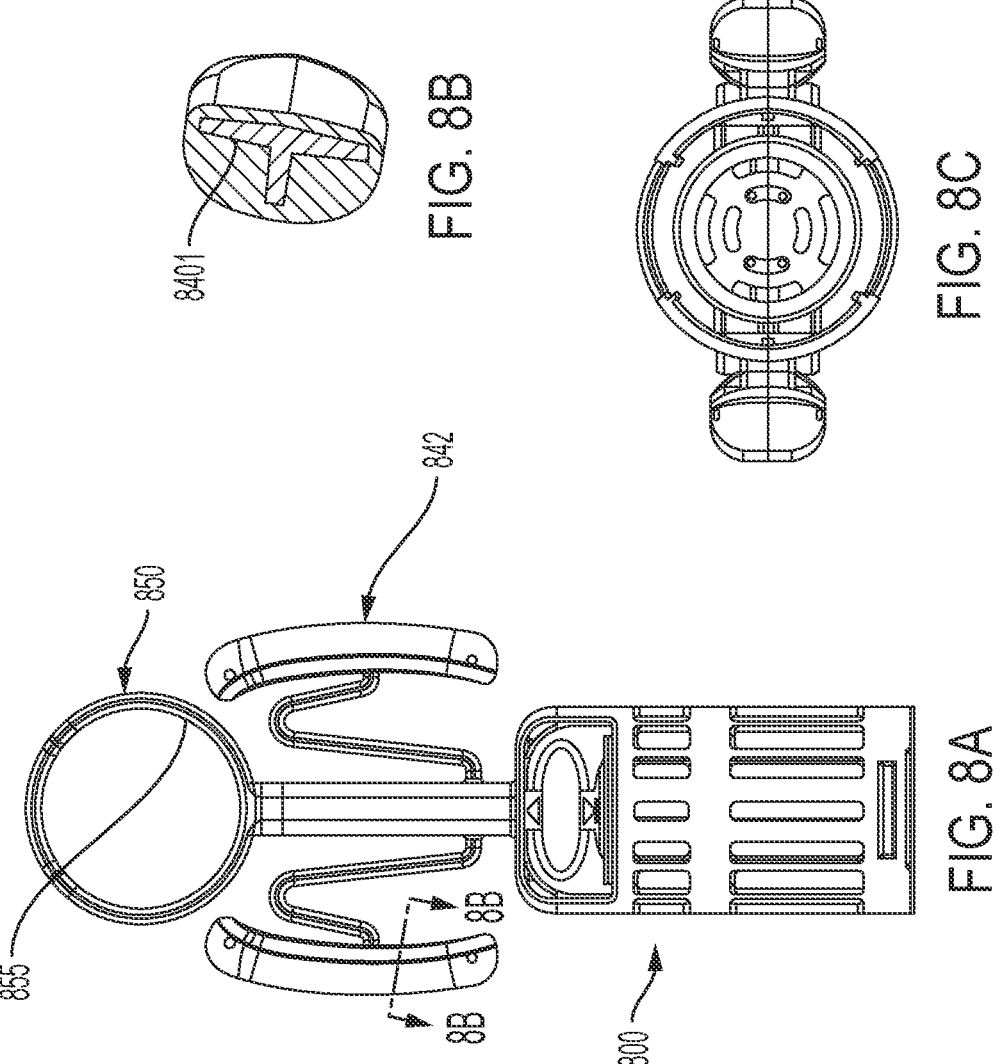
FIG. 8B
FIG. 8C
FIG. 8A

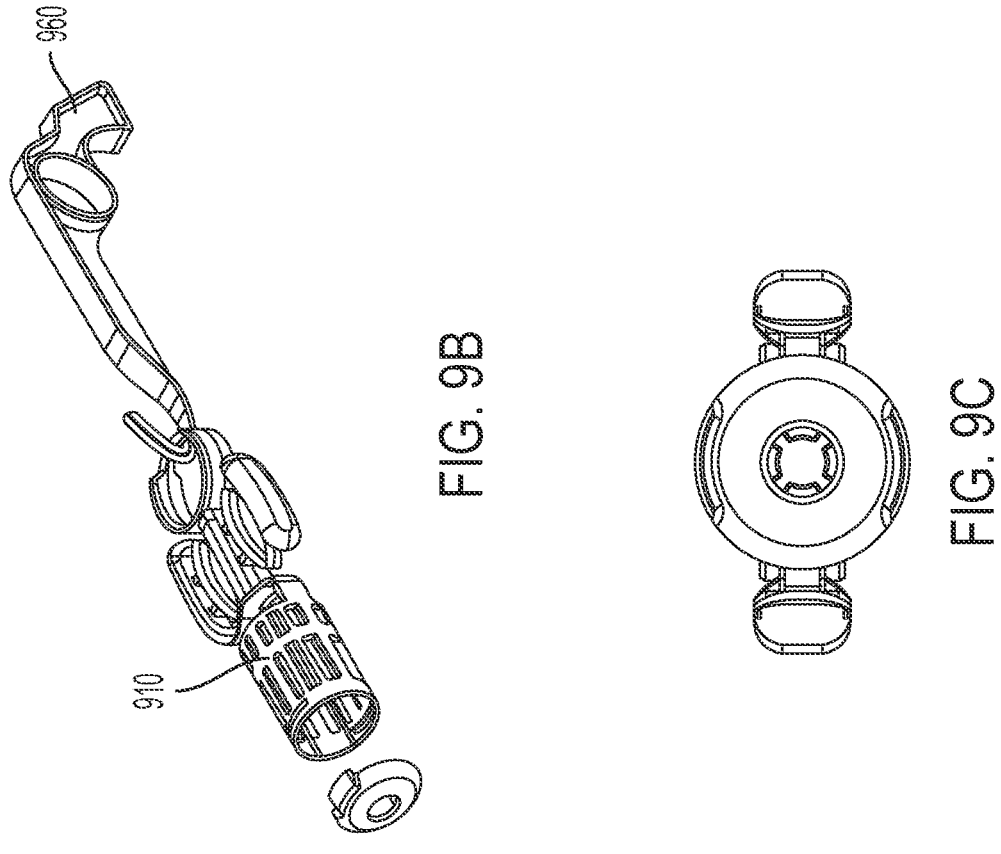
FIG. 9B
FIG. 9C
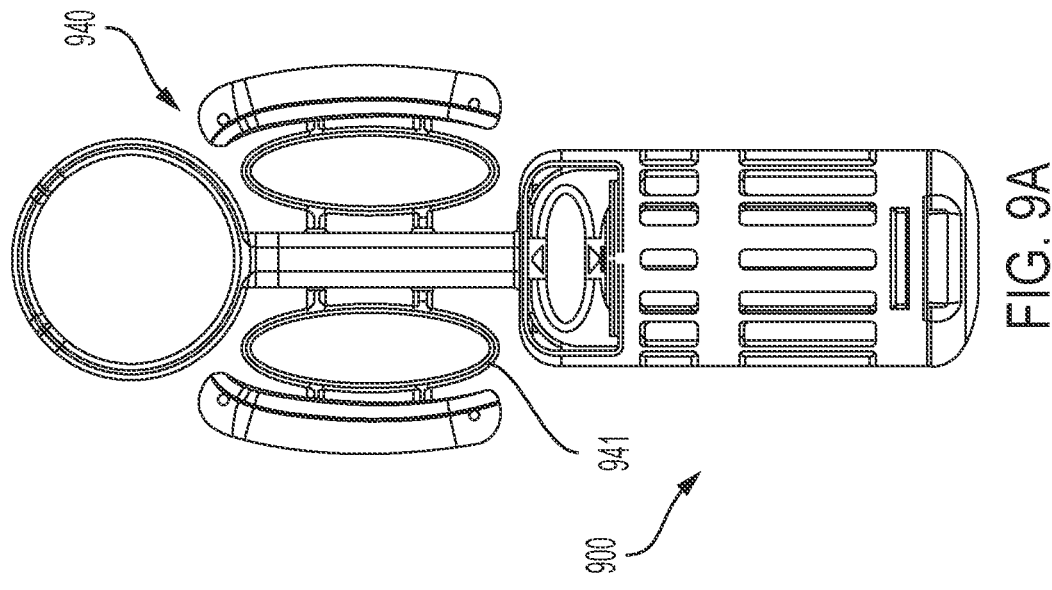
FIG. 9A

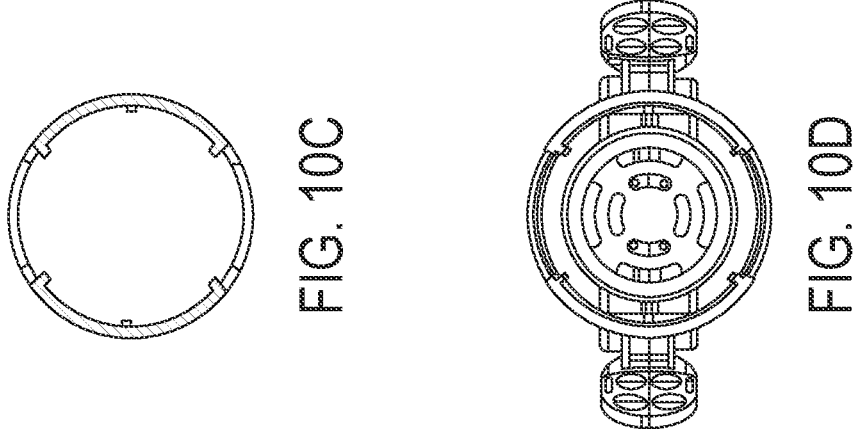
FIG. 10C
FIG. 10D
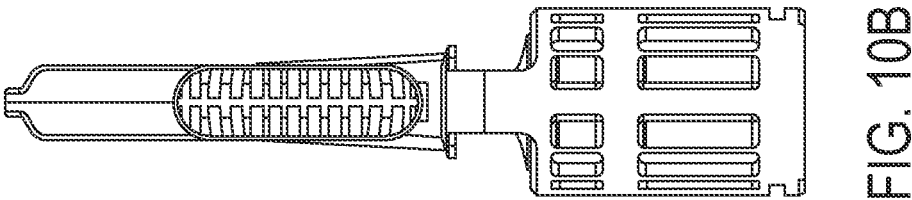
FIG. 10B
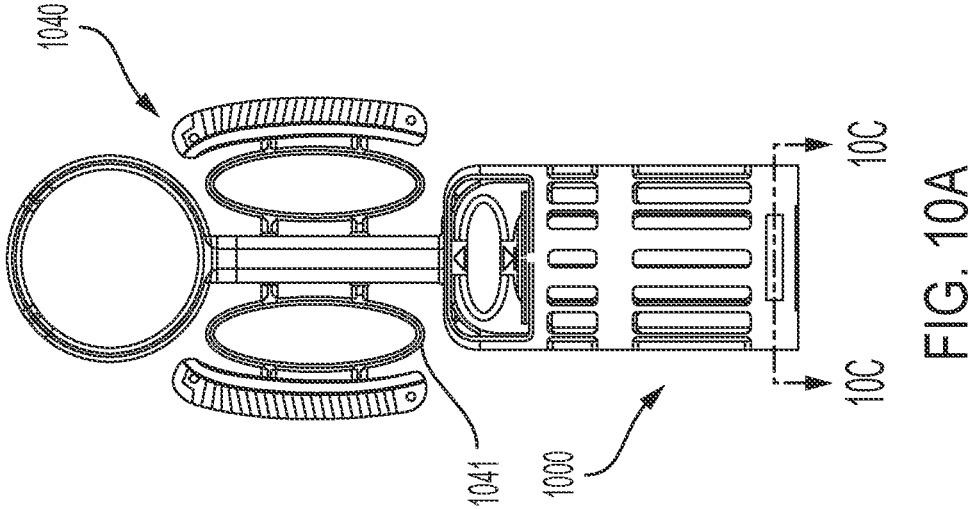
FIG. 10A

1260

SEE FIG. 13E

13D

13D

SEE FIG. 13B

1361

1360

1362

SEE FIG. 14D

SEE FIG. 18B

MEDICAMENT DELIVERY SYSTEM, AND ASSOCIATED METHOD

CROSS REFERENCE TO RELATED APPLICATION

This application claims the benefit of U.S. Provisional Patent Application No. 63/152,096, filed Feb. 22, 2021, which is expressly incorporated herein by reference in its entirety.

BACKGROUND

Field of the Disclosure

The present disclosure relates to medicament delivery systems and methods and, more particularly to a medicament delivery system and method for making and using the same, with the medicament delivery system having an osmotic delivery device or an erodible object engaged with a retention arrangement for removably retaining the osmotic delivery device or erodible object within a bodily orifice for medicament delivery thereto.

Description of Related Art

Some medicaments for animals are required to be delivered over an extended period of time, as opposed to individual doses. Heretofore, such medicaments can be delivered to the animal through a bodily orifice such as, for example, a vaginal orifice. For instance, vaginal delivery of the medicament may function to control the breeding cycle of the animal, which may be for example porcine, bovine and/or ovine. Some prior art intra-vaginal medicament delivery devices implement a physical framework having a medicament-releasing portion engaged with and surrounding a portion of the physical framework such that the medicament-releasing portion is externally exposed. The medicament-releasing portion may be configured to release, for example, a contraceptive drug over time. Limitations associated with such prior art intra-vaginal medicament delivery devices include lack of flexibility with the drug release form, passive diffusion, reduced drug loading, and drug remnants after first use that allow ill-advised reuse.

As such, there exists a need for an improved medicament delivery system for delivering a medicament within a bodily orifice of an animal.

SUMMARY

The above and other needs are met by aspects of the present disclosure which includes, without limitation, the following example embodiments and, in one particular aspect, provides an intra-orifice medicament delivery system, including a housing having a chamber wall defining an inner chamber extending along a longitudinal axis, wherein the chamber wall further defines one or more openings extending from the chamber through the chamber wall. A retention arrangement is engaged with and extends from the housing, wherein the retention arrangement is adapted to removably retain the housing within a bodily orifice defined by an orifice wall. An osmotic delivery device is disposed within the chamber and includes an osmogen portion and medicament-including portion disposed within a semipermeable membrane. The osmogen portion is arranged to expand and to apply pressure to the medicament-including portion in response to absorption of a liquid from within the bodily orifice permeating through the semipermeable membrane. The medicament-including portion is arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice.

Another aspect of the present disclosure provides a method of forming an intra-orifice medicament delivery system, including forming a housing having a chamber wall defining an inner chamber extending along a longitudinal axis, such that the chamber wall defines one or more openings extending from the chamber through the chamber wall; engaging a retention arrangement with the housing such that the retention arrangement extends from the housing and is adapted to removably retain the housing within a bodily orifice defined by an orifice wall; and disposing an osmotic delivery device, including an osmogen portion and medicament-including portion disposed within a semipermeable membrane, within the chamber, such that the osmogen portion is arranged to expand and to apply pressure to the medicament-including portion in response to absorption of a liquid from within the bodily orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice.

Yet another aspect of the present disclosure provides an intra-orifice medicament delivery system, including a housing having a chamber wall defining an inner chamber extending along a longitudinal axis, wherein the chamber wall further defines one or more openings extending from the chamber through the chamber wall. A retention arrangement is engaged with and extends from the housing, wherein the retention arrangement is adapted to removably retain the housing within a bodily orifice defined by an orifice wall. An erodible object is disposed within the chamber and includes a medicament component. The erodible object is arranged to dissolve in response to interaction with a liquid from within the bodily orifice, thereby releasing the medicament component to exit the housing through the one or more openings such that the medicament component is delivered into the bodily orifice.

Still yet another aspect of the present disclosure provides a method of forming an intra-orifice medicament delivery system, including forming a housing having a chamber wall defining an inner chamber extending along a longitudinal axis, such that the chamber wall defines one or more openings extending from the chamber through the chamber wall; engaging a retention arrangement with the housing such that the retention arrangement extends from the housing and is adapted to removably retain the housing within a bodily orifice defined by an orifice wall; and disposing an erodible object, including a medicament component, within the chamber, such that the erodible object is arranged to dissolve in response to interaction with a liquid from within the bodily orifice, thereby releasing the medicament component to exit the housing through the one or more openings for delivery into the bodily orifice.

The present disclosure thus includes, without limitation, the following example embodiments:

Example Embodiment 1: An intra-orifice medicament delivery system, comprising a housing having a chamber wall defining an inner chamber extending along a longitudinal axis, the chamber wall further defining one or more openings extending from the chamber through the chamber wall; a retention arrangement engaged with and extending from the housing, the retention arrangement being adapted to removably retain the housing within a bodily orifice defined by an orifice wall; and an osmotic delivery device disposed within the chamber and including an osmogen portion and medicament-including portion disposed within a semipermeable membrane, the osmogen portion being arranged to expand and to apply pressure to the medicament-including portion in response to absorption of a liquid from within the bodily orifice permeating through the semipermeable membrane, the medicament-including portion being arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice.

Example Embodiment 2: The system of any preceding example embodiment, or combinations thereof, comprising a housing removal arrangement engaged with the housing or the retention arrangement, the housing removal arrangement being adapted to facilitate removal of the housing from the bodily orifice.

Example Embodiment 3: The system of any preceding example embodiment, or combinations thereof, wherein the housing removal arrangement is engaged with the housing via a stem arranged therebetween, the stem extending along the longitudinal axis.

Example Embodiment 4: The system of any preceding example embodiment, or combinations thereof, wherein the housing removal arrangement includes a ring member.

Example Embodiment 5: The system of any preceding example embodiment, or combinations thereof, wherein the housing removal arrangement further includes an elongate handle having a distal end including a hook member arranged to engage the ring member for facilitating removal of the housing from the bodily orifice.

Example Embodiment 6: The system of any preceding example embodiment, or combinations thereof, wherein the retention arrangement is serially engaged between the housing removal arrangement and the housing.

Example Embodiment 7: The system of any preceding example embodiment, or combinations thereof, wherein the retention arrangement is engaged with a first end of the housing and the housing removal arrangement is engaged with a second end of the housing.

Example Embodiment 8: The system of any preceding example embodiment, or combinations thereof, wherein the retention arrangement is engaged with the stem between the housing removal arrangement and the housing.

Example Embodiment 9: The system of any preceding example embodiment, or combinations thereof, wherein the retention arrangement includes one or more retention members engaged with and extending away from the housing or the stem, such that the one or more retention members is arranged to be biased toward and into engagement with the orifice wall for retaining the housing within the bodily orifice.

Example Embodiment 10: The system of any preceding example embodiment, or combinations thereof, wherein the one or more retention members is arranged in a cantilevered arrangement in relation to the housing or the stem.

Example Embodiment 11: The system of any preceding example embodiment, or combinations thereof, wherein the one or more retention members is flexible or wherein the engagement between the one or more retention members and the housing or the stem is flexible, the flexibility associated with the one or more retention members biasing the one or more retention members into interaction with the orifice wall for retaining the housing within the bodily orifice, or facilitating disengagement of the one or more retention members from the orifice wall for removing the housing from the bodily orifice.

Example Embodiment 12: The system of any preceding example embodiment, or combinations thereof, wherein distal end of the one or more retention members is rounded or includes a rounded member engaged therewith so as to prevent perforation of the orifice wall by the distal ends or to facilitate removal of the housing from the bodily orifice.

Example Embodiment 13: The system of any preceding example embodiment, or combinations thereof, wherein the housing defines a maximum diameter perpendicular to the longitudinal axis, and wherein distal end of the one or more retention members or the rounded member engaged therewith extends outwardly from the stem for greater than the maximum diameter of the housing.

Example Embodiment 14: The system of any preceding example embodiment, or combinations thereof, wherein the membrane about the medicament-including portion defines one or more pores, the medicament emitted by the medicament-including portion exiting the membrane via the one or more pores.

Example Embodiment 15: The system of any preceding example embodiment, or combinations thereof, wherein the membrane, the medicament-including portion, or the osmogen portion is arranged to cause the medicament-including portion to emit the medicament at a predetermined rate.

Example Embodiment 16: The system of any preceding example embodiment, or combinations thereof, wherein the one or more openings defined by the chamber wall and extending from the chamber through the chamber wall define a relatively larger open area about an outer surface of the chamber wall and a relatively smaller open area about an inner surface of the chamber wall so as to funnel liquid from the bodily orifice into the chamber.

Example Embodiment 17: The system of any preceding example embodiment, or combinations thereof, comprising one or more protrusions extending from the chamber wall into the chamber, the one or more protrusions facilitating spacing of the osmotic delivery device away from the chamber wall to facilitate circulation of liquid about the osmotic delivery device.

Example Embodiment 18: The system of any preceding example embodiment, or combinations thereof, wherein the chamber wall is substantially cylindrical and has opposing first and second ends, wherein the housing includes an end wall engaged with each opposing end, and wherein one of the end walls defines one or more openings.

Example Embodiment 19: The system of any preceding example embodiment, or combinations thereof, wherein the medicament-including portion of the osmotic delivery device is disposed adjacent to the one of the end walls defining the one or more openings.

Example Embodiment 20: The system of any preceding example embodiment, or combinations thereof, comprising a biasing arrangement engaged between the chamber wall and the osmotic delivery device, the biasing arrangement being arranged to bias the osmotic delivery device against the one of the end walls so as to facilitate emission of the medicament from the medicament-including portion through the one or more openings defined by the one of the end walls.

Example Embodiment 21: The system of any preceding example embodiment, or combinations thereof, wherein the osmogen portion is disposed in contact with the medicament-including portion, and wherein the semipermeable membrane comprises a coating applied about the osmogen portion and the medicament-including portion.

Example Embodiment 22: The system of any preceding example embodiment, or combinations thereof, wherein the housing comprises two interlocking portions containing the osmotic delivery device within the chamber defined thereby upon engagement therebetween.

Example Embodiment 23: The system of any preceding example embodiment, or combinations thereof, wherein the medicament-including portion includes a steroid, a hormone, a cytokine signaling molecule, a pain management drug, a cardiovascular drug, an immunomodulating agent, a protein, a peptide, a glycoprotein, or combinations thereof.

Example Embodiment 24: The system of any preceding example embodiment, or combinations thereof, wherein the osmogen portion includes magnesium stearate.

Example Embodiment 25: A method of forming an intraorifice medicament delivery system, comprising forming a housing having a chamber wall defining an inner chamber extending along a longitudinal axis, such that the chamber wall defines one or more openings extending from the chamber through the chamber wall; engaging a retention arrangement with the housing such that the retention arrangement extends from the housing and is adapted to removably retain the housing within a bodily orifice defined by an orifice wall; and disposing an osmotic delivery device, including an osmogen portion and medicament-including portion disposed within a semipermeable membrane, within the chamber, such that the osmogen portion is arranged to expand and to apply pressure to the medicament-including portion in response to absorption of a liquid from within the bodily orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice.

Example Embodiment 26: The method of any preceding example embodiment, or combinations thereof, comprising engaging a housing removal arrangement with the housing or the retention arrangement, wherein the housing removal arrangement is adapted to facilitate removal of the housing from the bodily orifice.

Example Embodiment 27: The method of any preceding example embodiment, or combinations thereof, wherein engaging the housing removal arrangement comprises engaging the housing removal arrangement with the housing via a stem arranged therebetween and extending along the longitudinal axis.

Example Embodiment 28: The method of any preceding example embodiment, or combinations thereof, wherein engaging the housing removal arrangement comprises engaging a ring member of the housing removal arrangement with the housing or the retention arrangement.

Example Embodiment 29: The method of any preceding example embodiment, or combinations thereof, comprising engaging the ring member of the housing removal arrangement with a distal end of an elongate handle, the distal end including a hook member arranged to engage the ring member for facilitating removal of the housing from the bodily orifice.

Example Embodiment 30: The method of any preceding example embodiment, or combinations thereof, wherein engaging the retention arrangement comprises serially engaging the retention arrangement between the housing removal arrangement and the housing.

Example Embodiment 31: The method of any preceding example embodiment, or combinations thereof, wherein engaging the retention arrangement comprises engaging the retention arrangement with a first end of the housing and engaging the housing removal arrangement with a second end of the housing.

Example Embodiment 32: The method of any preceding example embodiment, or combinations thereof, wherein engaging the retention arrangement comprises engaging the retention arrangement with the stem between the housing removal arrangement and the housing.

Example Embodiment 33: The method of any preceding example embodiment, or combinations thereof, wherein engaging the retention arrangement comprises engaging one or more retention members with and to extend away from the housing or the stem, such that the one or more retention members is arranged to be biased toward and into engagement with the orifice wall for retaining the housing within the bodily orifice.

Example Embodiment 34: The method of any preceding example embodiment, or combinations thereof, combinations thereof, comprising arranging the one or more retention members in a cantilevered arrangement in relation to the housing or the stem.

Example Embodiment 35: The method of any preceding example embodiment, or combinations thereof, comprising rounding the distal end of the one or more retention members or engaging a rounded member with each of the distal ends so as to prevent perforation of the orifice wall by the distal ends or to facilitate removal of the housing from the bodily orifice.

Example Embodiment 36: The method of any preceding example embodiment, or combinations thereof, wherein the housing defines a maximum diameter perpendicular to the longitudinal axis, and wherein rounding the distal end or engaging the rounded member comprises rounding the distal end or engaging the rounded member with each of the distal ends such that the distal end of the one or more retention members or the rounded member engaged therewith extends outwardly from the stem for greater than the maximum diameter of the housing.

Example Embodiment 37: The method of any preceding example embodiment, or combinations thereof, comprising forming the membrane defining one or more pores about the medicament-including portion such that the medicament emitted by the medicament-including portion exits the membrane via the one or more pores.

Example Embodiment 38: The method of any preceding example embodiment, or combinations thereof, comprising arranging the membrane, the medicament-including portion, or the osmogen portion to cause the medicament-including portion to emit the medicament at a predetermined rate.

Example Embodiment 39: The method of any preceding example embodiment, or combinations thereof, comprising forming the one or more openings defined by the chamber wall such that the one or more openings define a relatively larger open area about an outer surface of the chamber wall and a relatively smaller open area about an inner surface of the chamber wall.

Example Embodiment 40: The method of any preceding example embodiment, or combinations thereof, comprising forming one or more protrusions extending from the chamber wall into the chamber, the one or more protrusions facilitating spacing of the osmotic delivery device away from the chamber wall to facilitate circulation of liquid about the osmotic delivery device.

Example Embodiment 41: The method of any preceding example embodiment, or combinations thereof, wherein forming the housing comprises forming the housing such that the chamber wall is substantially cylindrical and has opposing first and second ends, and engaging an end wall with each opposing end, wherein one of the end walls defines one or more openings.

Example Embodiment 42: The method of any preceding example embodiment, or combinations thereof, wherein disposing the osmotic delivery device comprises disposing the osmotic delivery device within the chamber such that the medicament-including portion thereof is disposed adjacent to the one of the end walls defining the one or more openings.

Example Embodiment 43: The method of any preceding example embodiment, or combinations thereof, comprising engaging a biasing arrangement between the chamber wall and the osmotic delivery device, such that the biasing arrangement is arranged to bias the osmotic delivery device against the one of the end walls so as to facilitate emission of the medicament from the medicament-including portion through the one or more openings defined by the one of the end walls.

Example Embodiment 44: The method of any preceding example embodiment, or combinations thereof, wherein disposing the osmotic delivery device comprises disposing the osmotic delivery device within a first portion of the housing and engaging a second portion of the housing with the first portion such that the two portions interlock to contain the osmotic delivery device within the chamber defined thereby upon engagement therebetween.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE DRAWINGS

Figure 1A:
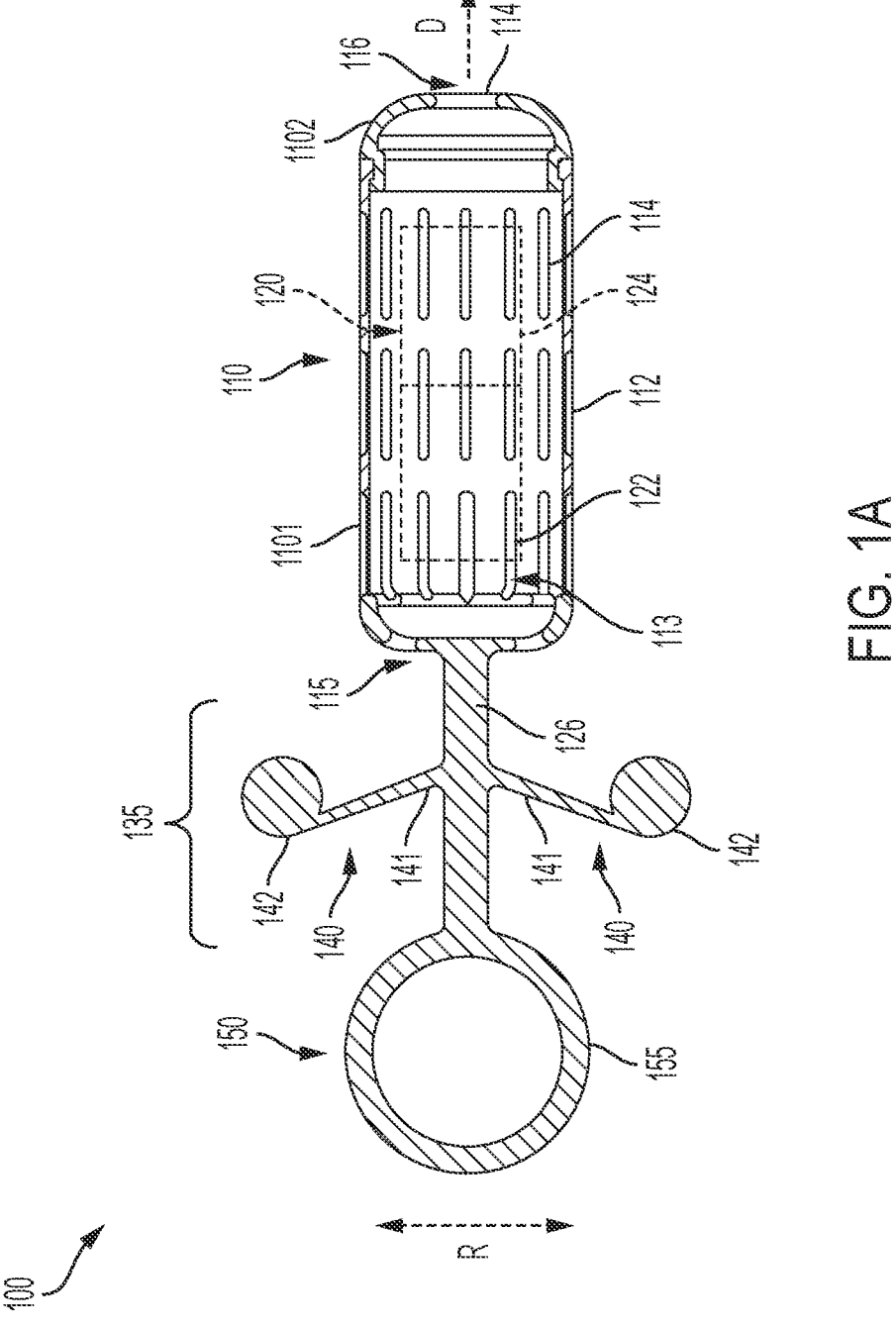
Figure 1B:
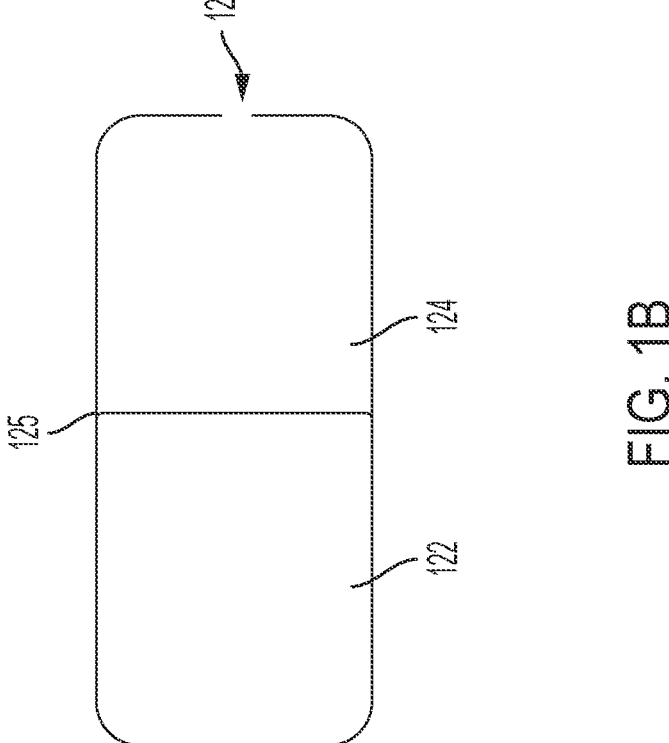
Figure 1B:
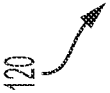
Figures 2A, 2B, 2C:
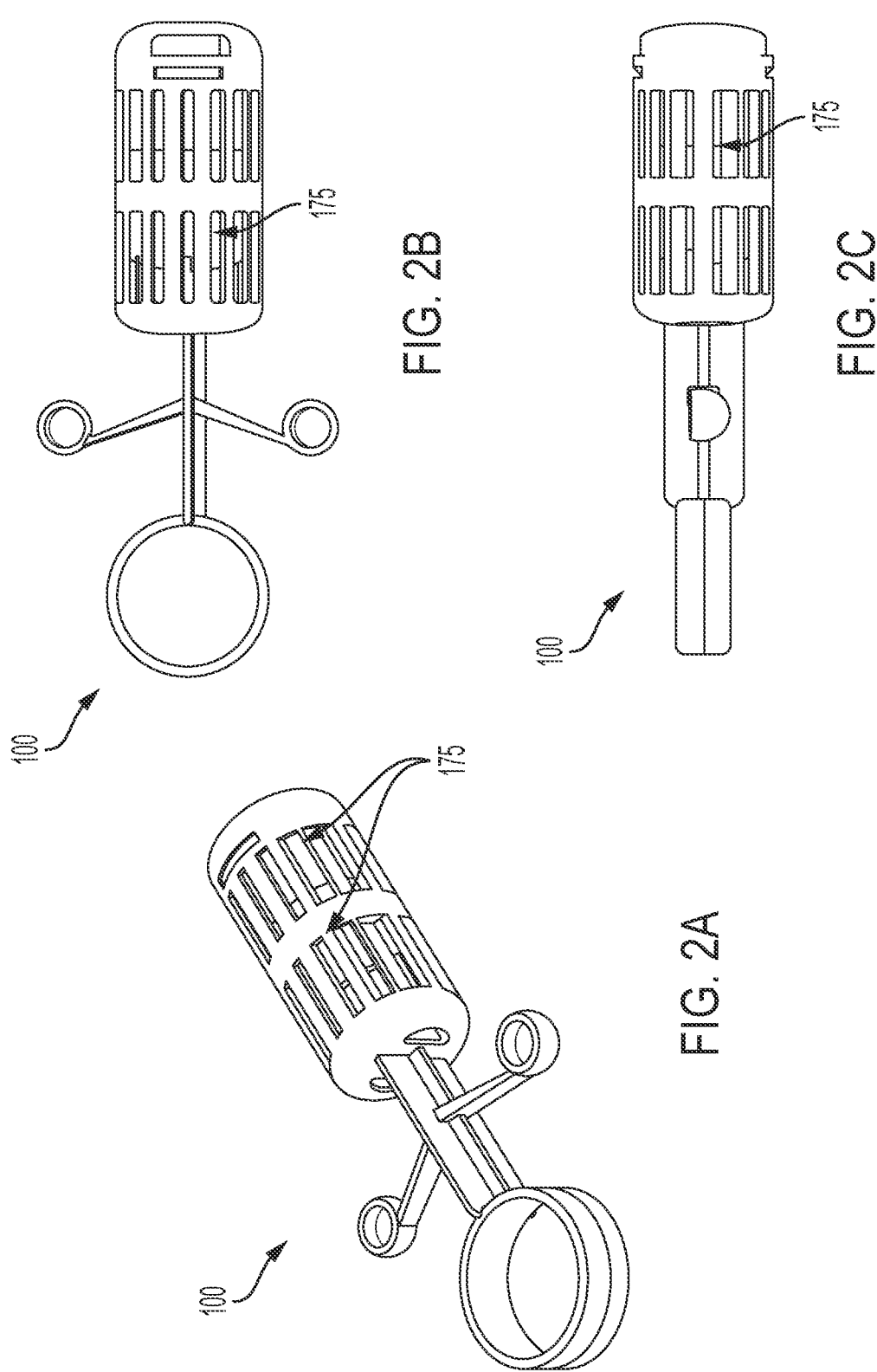
Figures 3A, 3B, 3C:
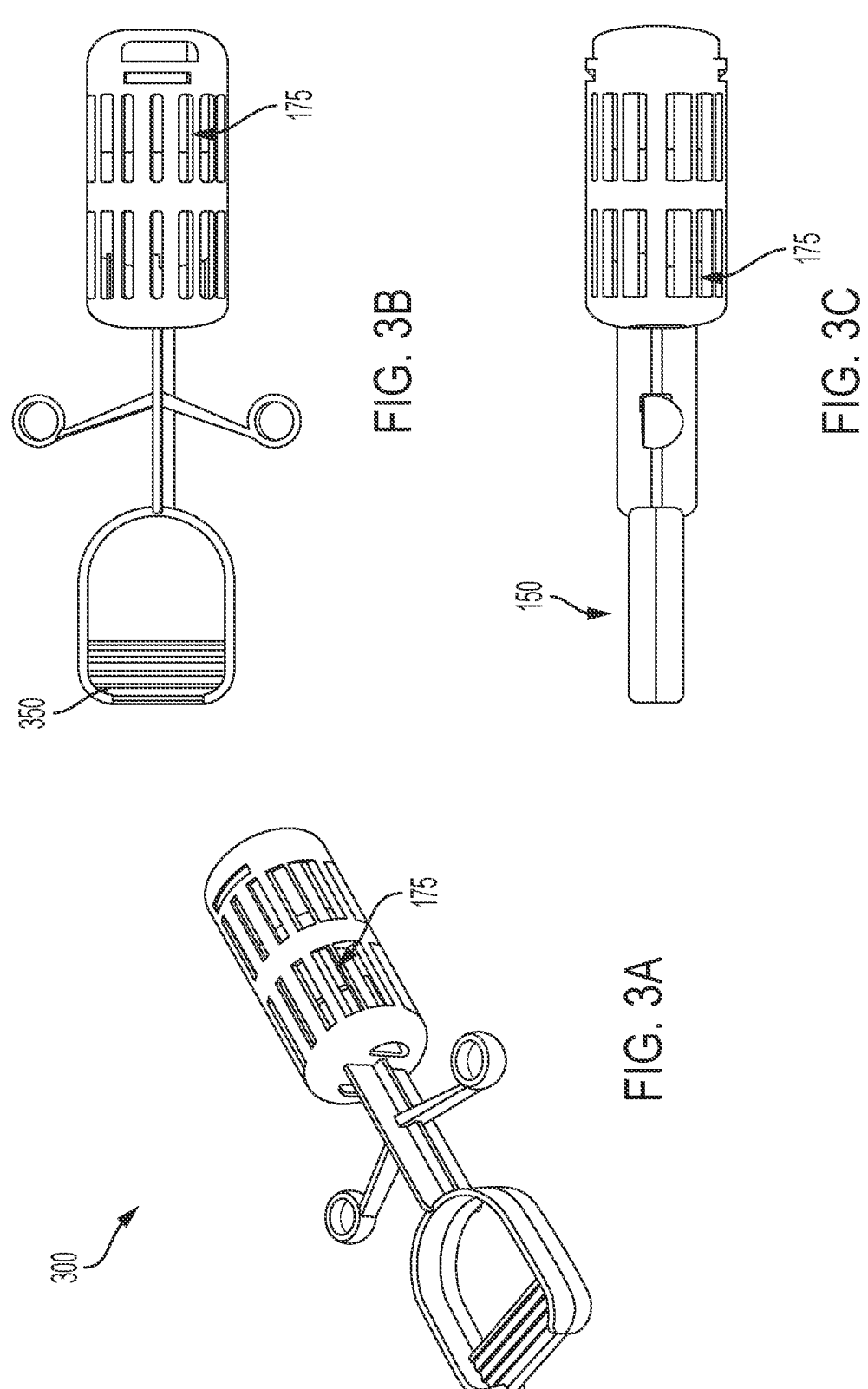
Figures 4A, 4B, 4C:
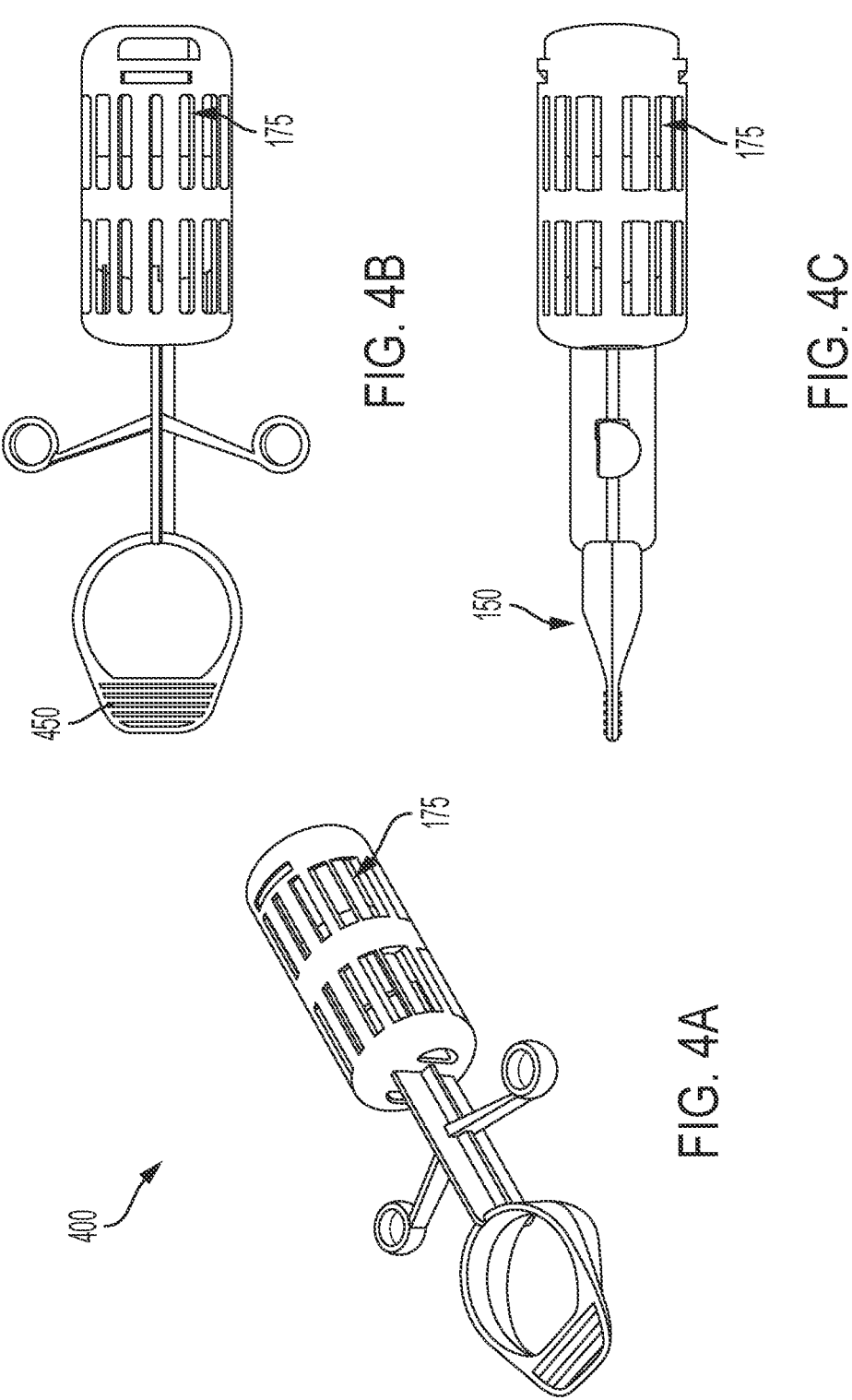
Figure 5B:
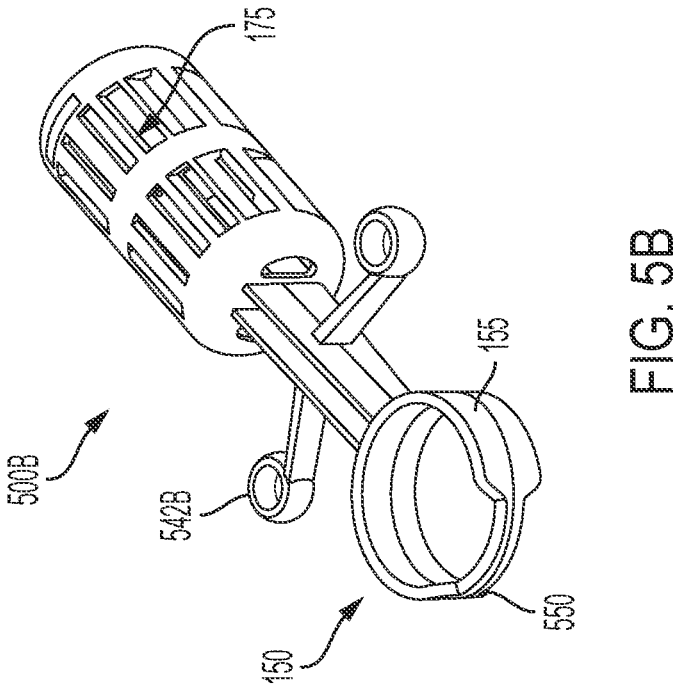
Figure 5A:
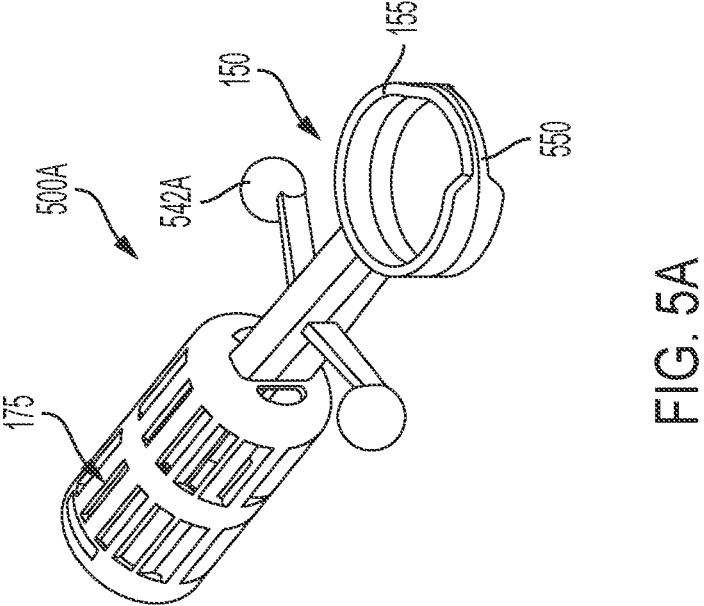
Figures 6A, 6B, 6C:
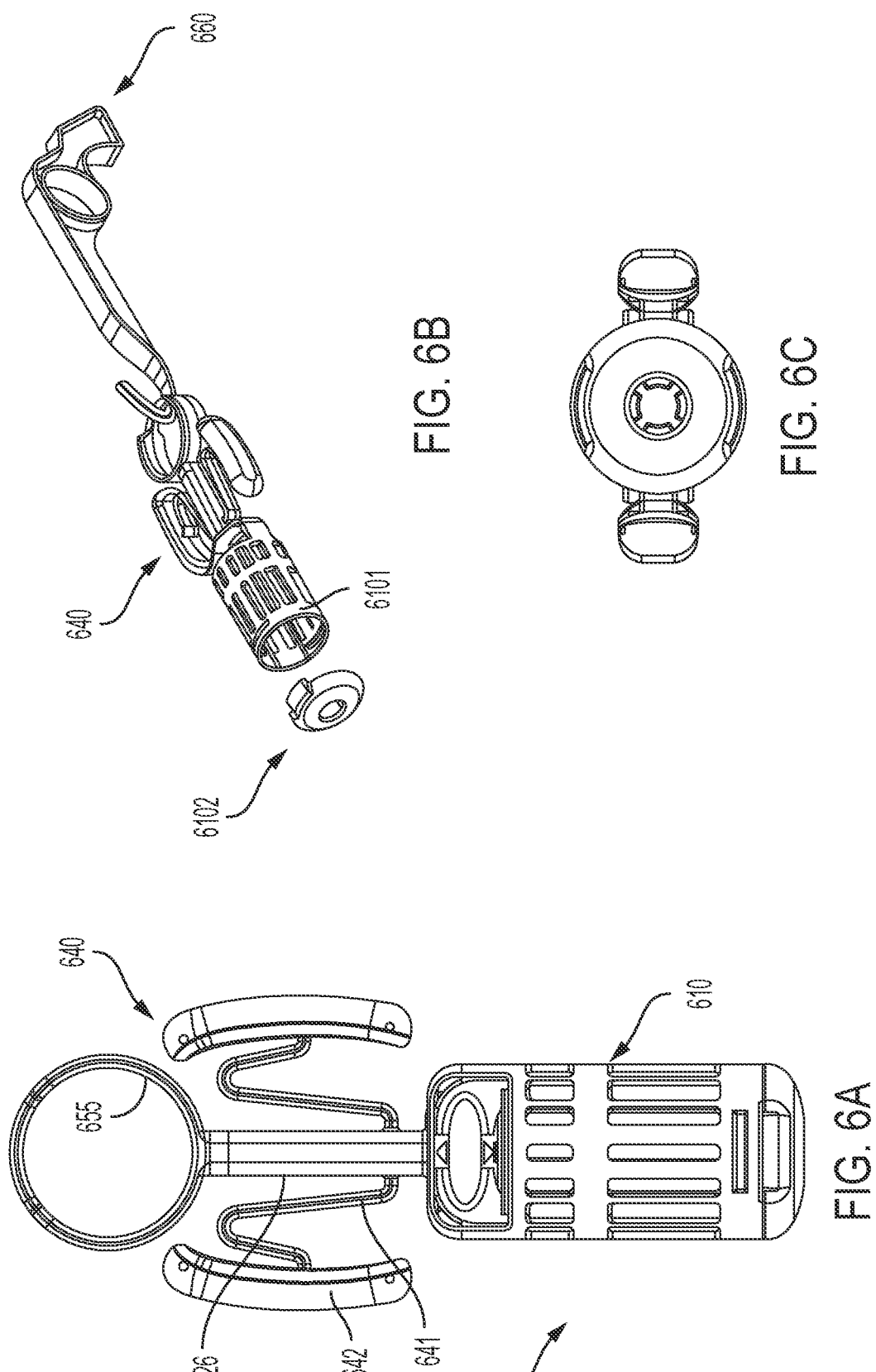
Figure 11D:
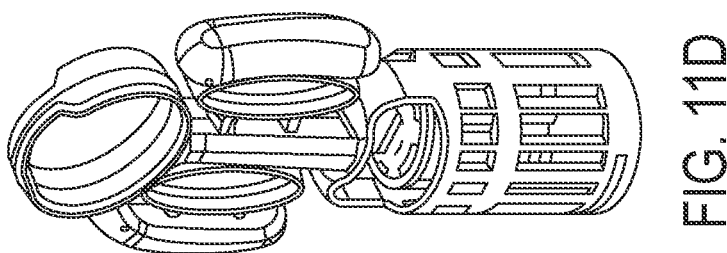
Figure 11B:
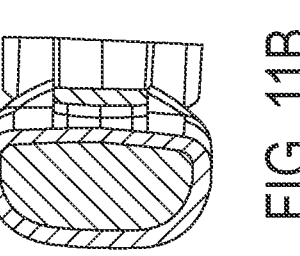
Figure 11C:
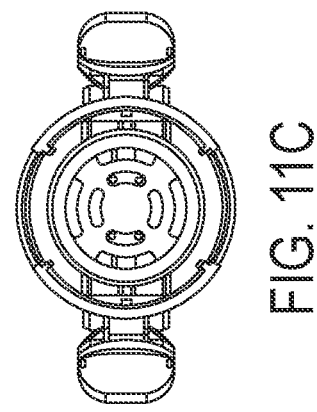
Figure 11A:
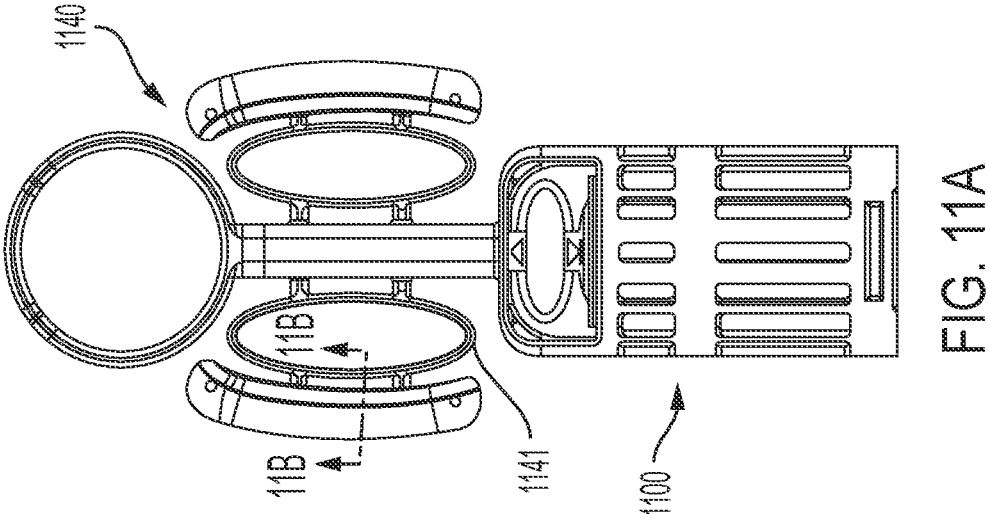
Figures 12A, 12B, 12C, 12D:
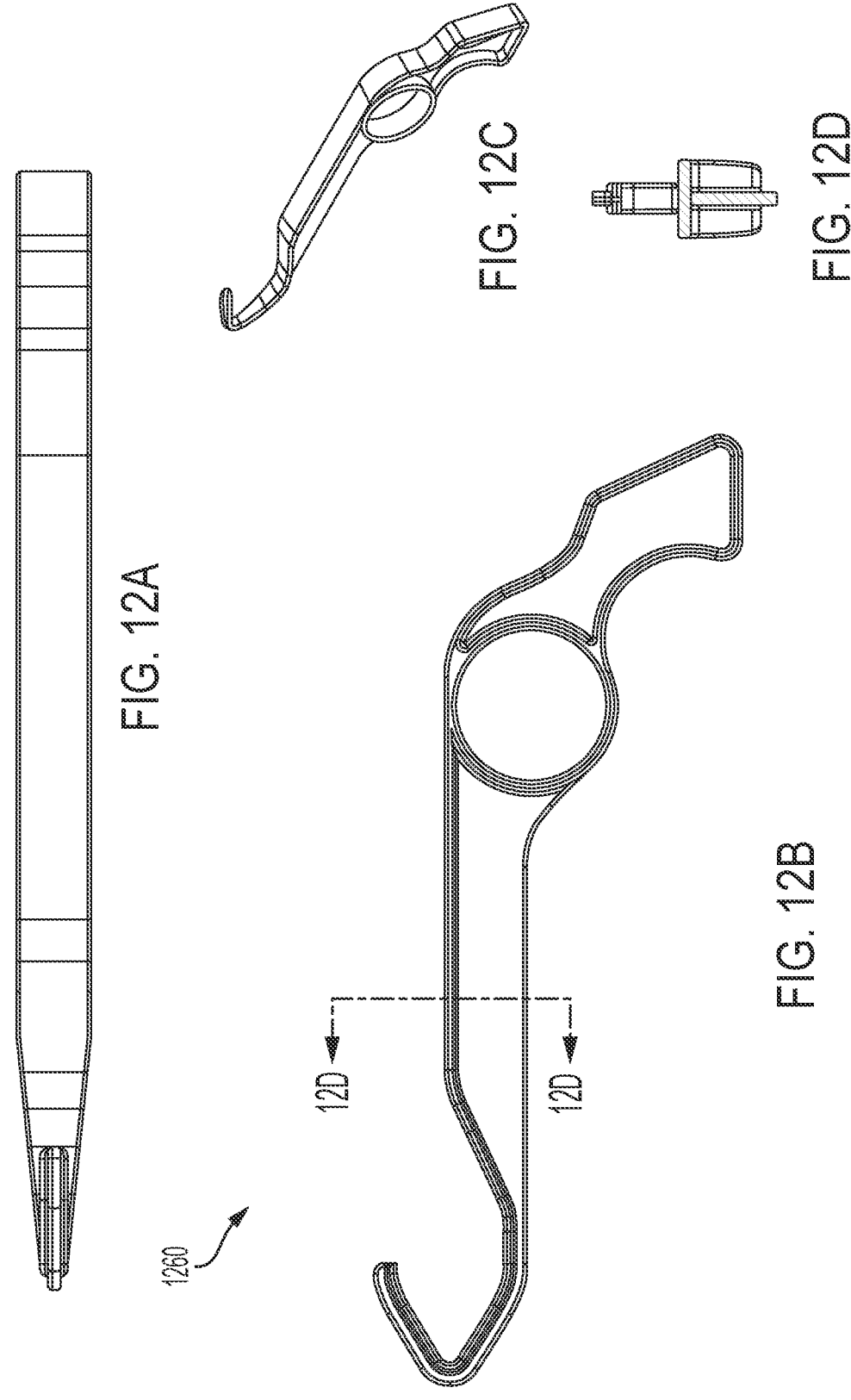
Figures 13A, 13B, 13C, 13D, 13E, 13F, 13G:
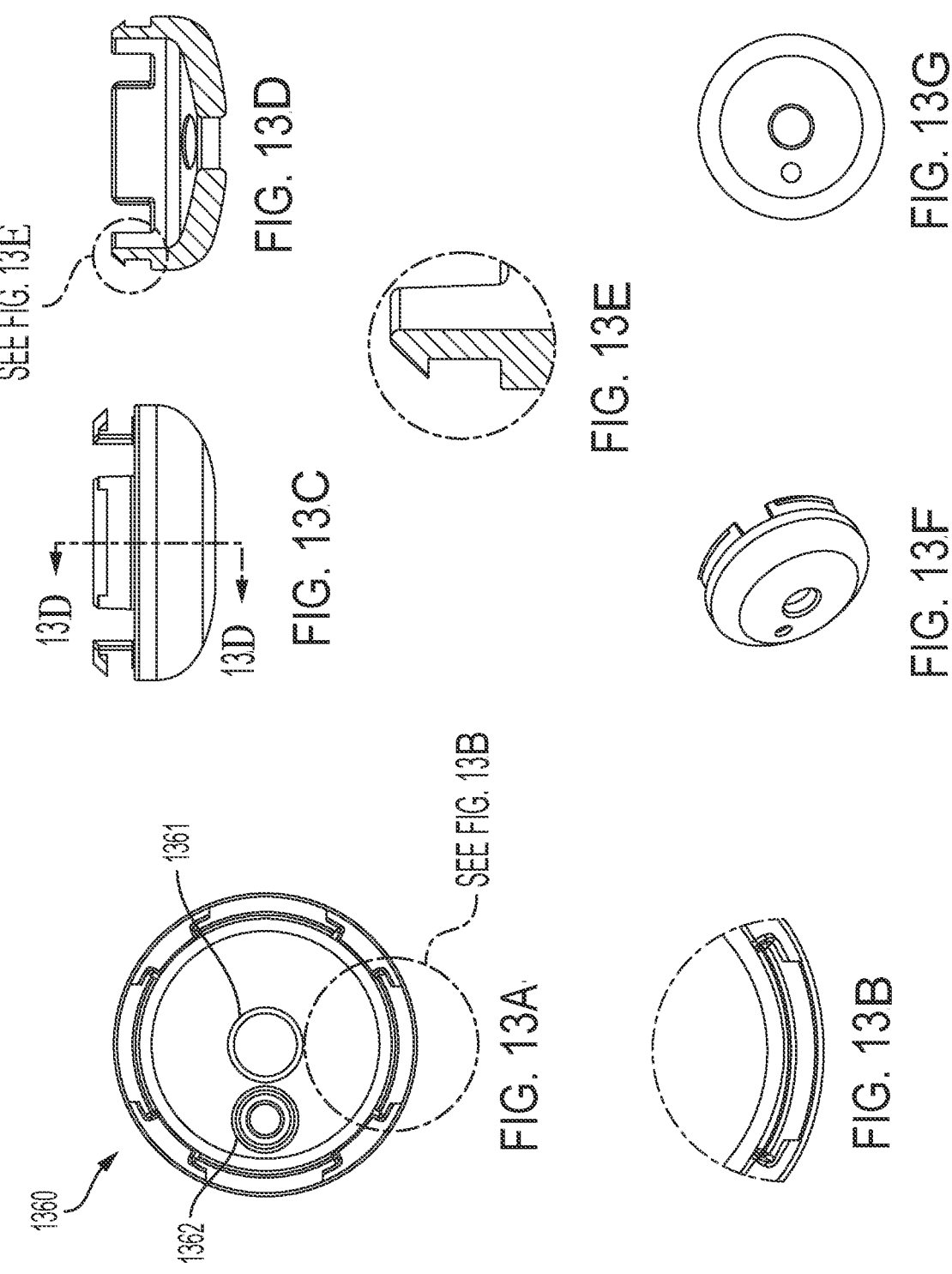
Figure 13H:
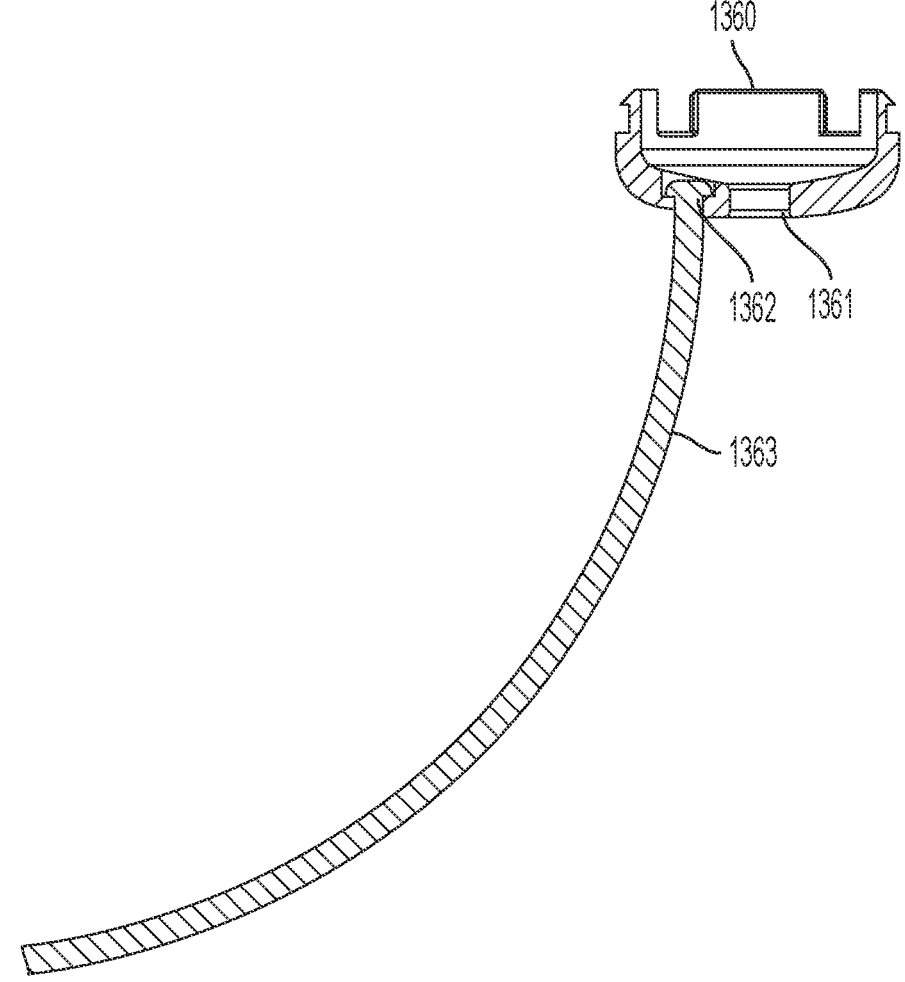
Figures 14A, 14B, 14C, 14D, 14E:
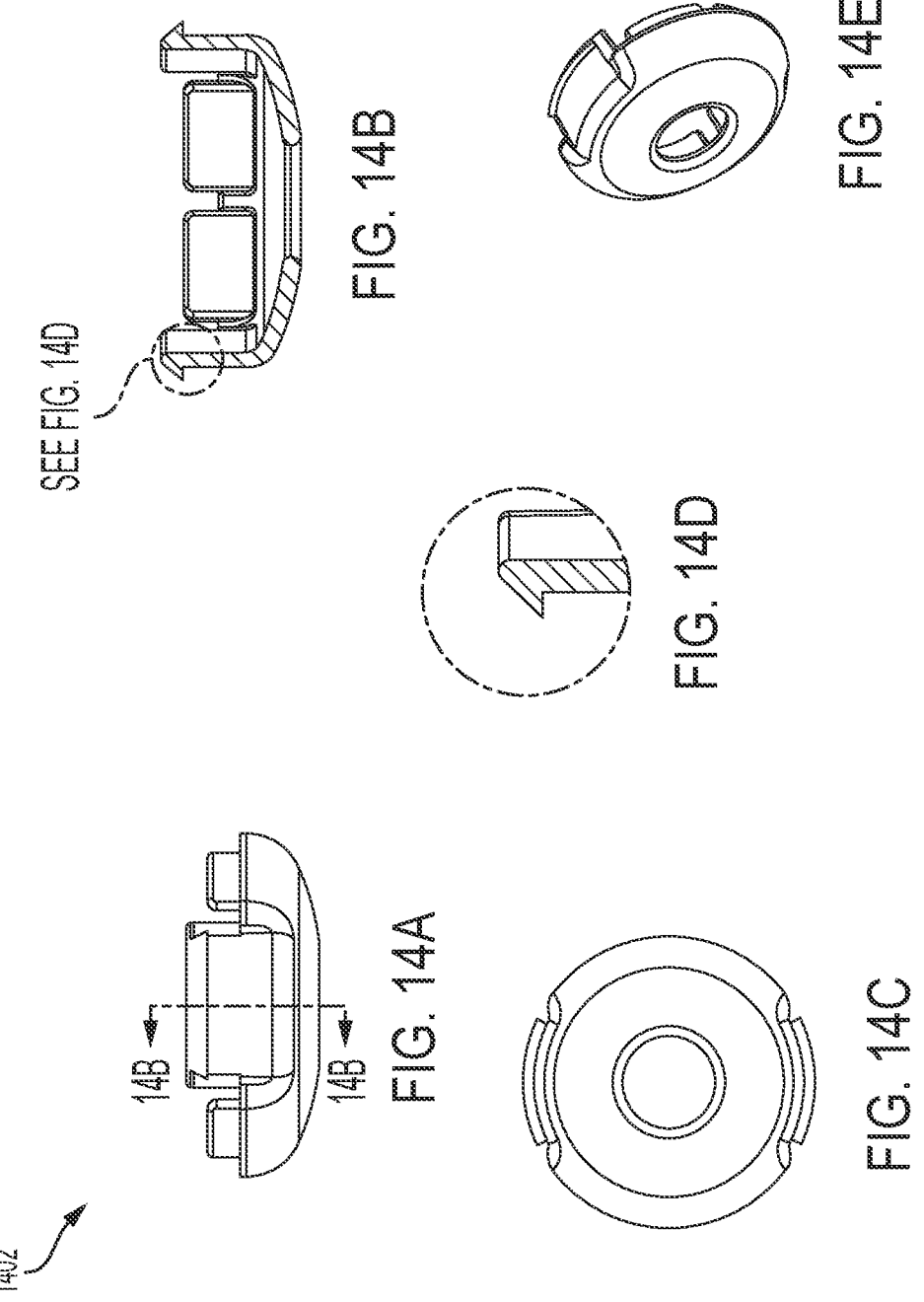
Figures 15A, 15B, 15C, 15D, 15E:
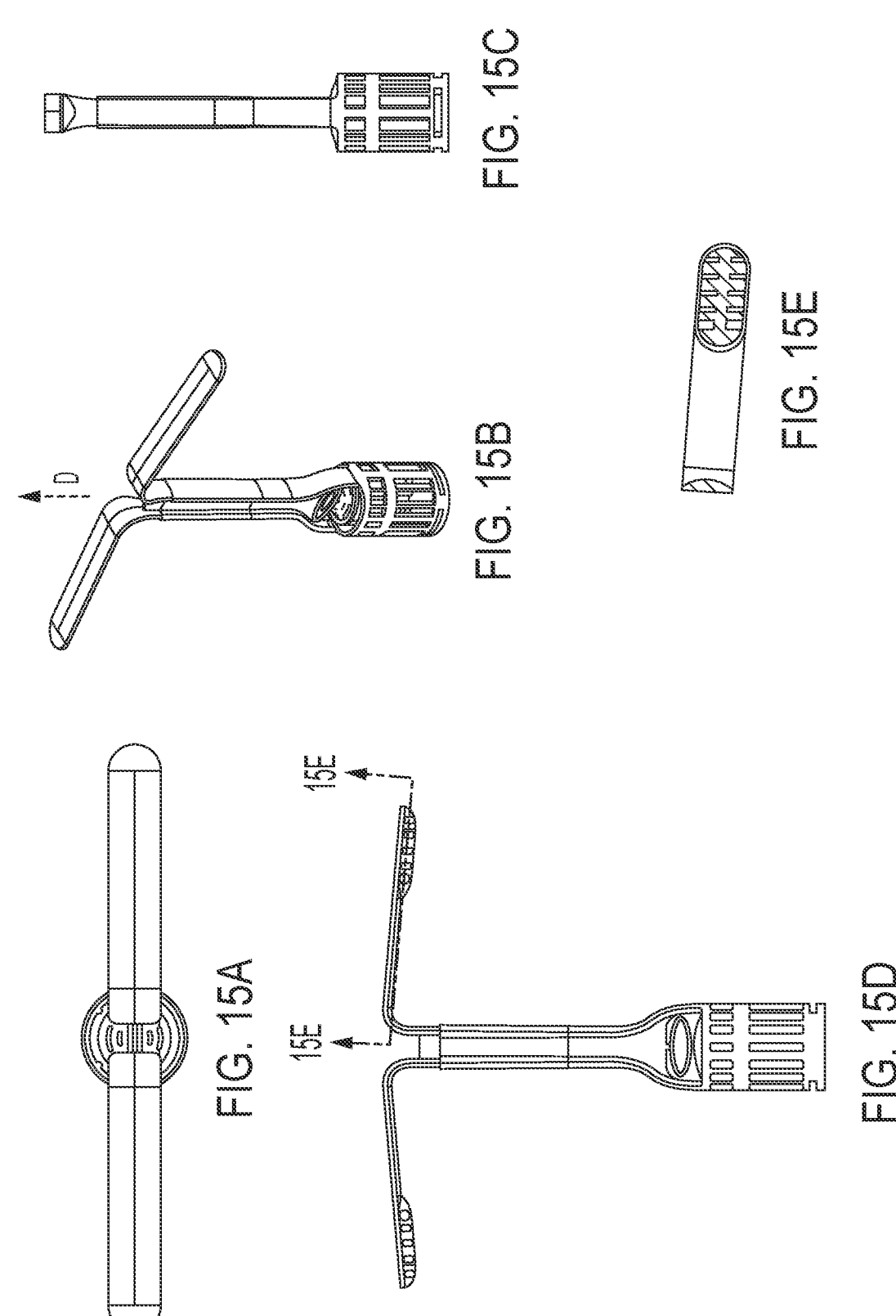
Figures 16A, 16B, 16C, 16D, 16E, 16F:
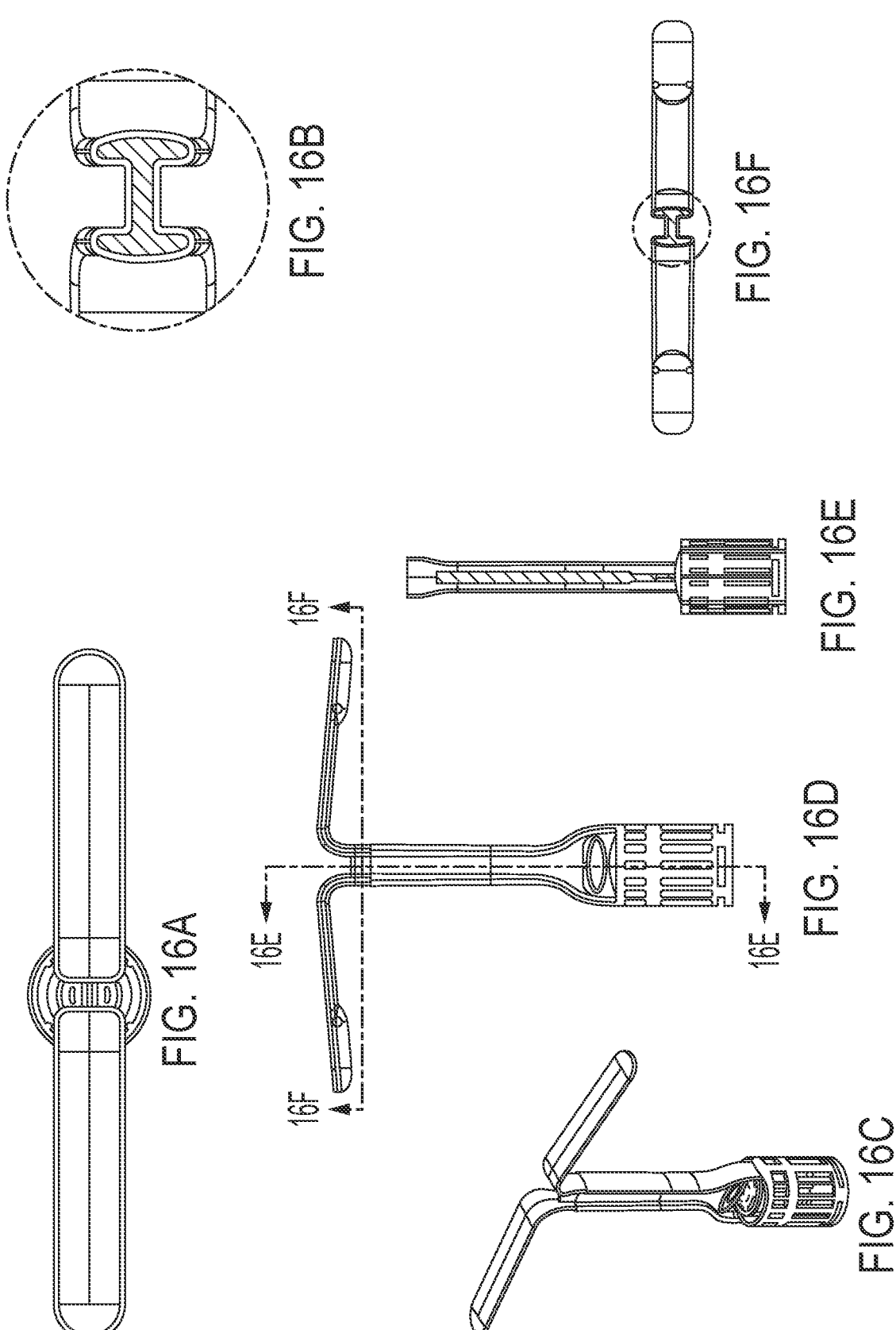
Figures 17A, 17B, 17C, 17D, 17E:
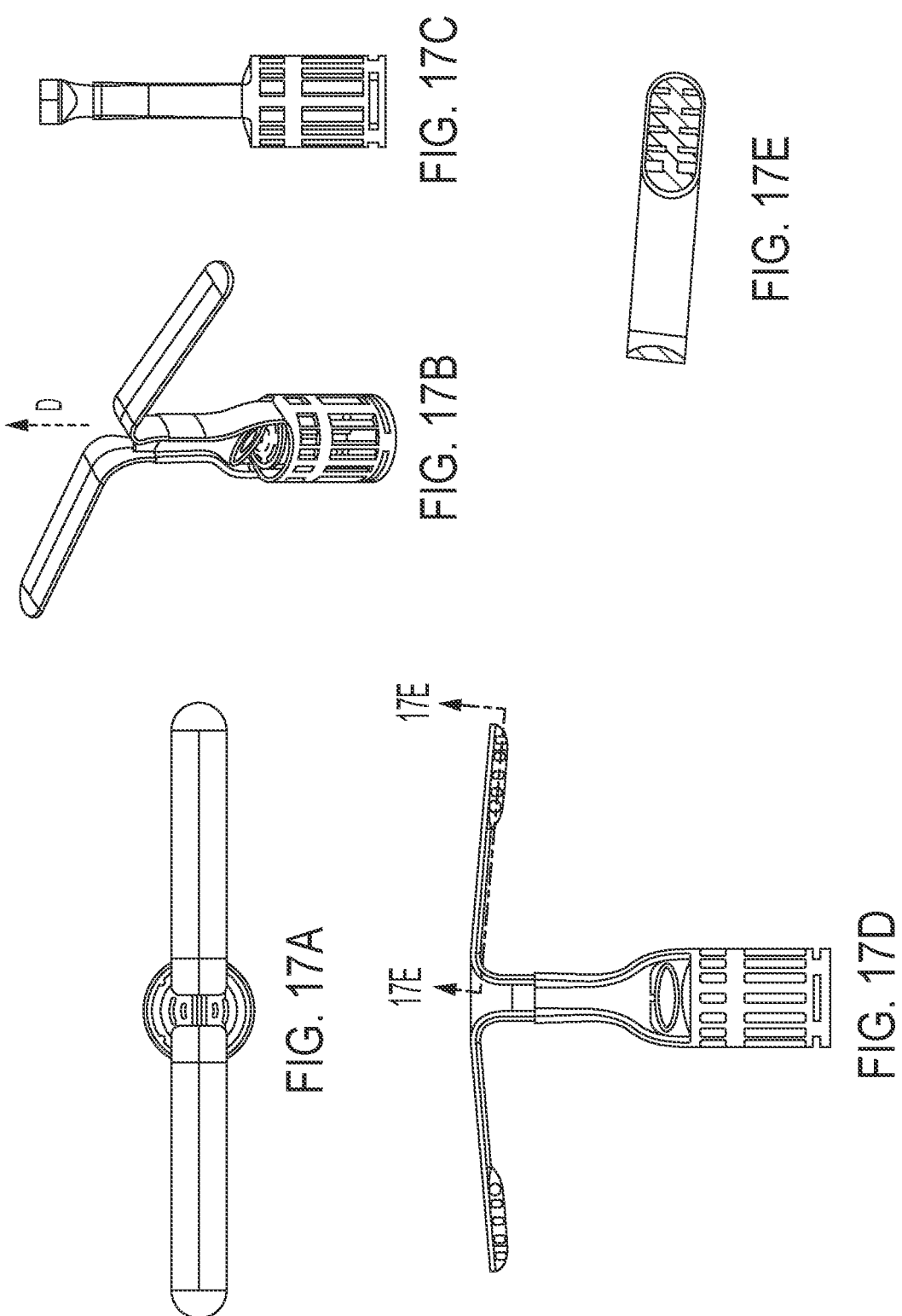
Figures 18A, 18B, 18C, 18D, 18E, 18F:
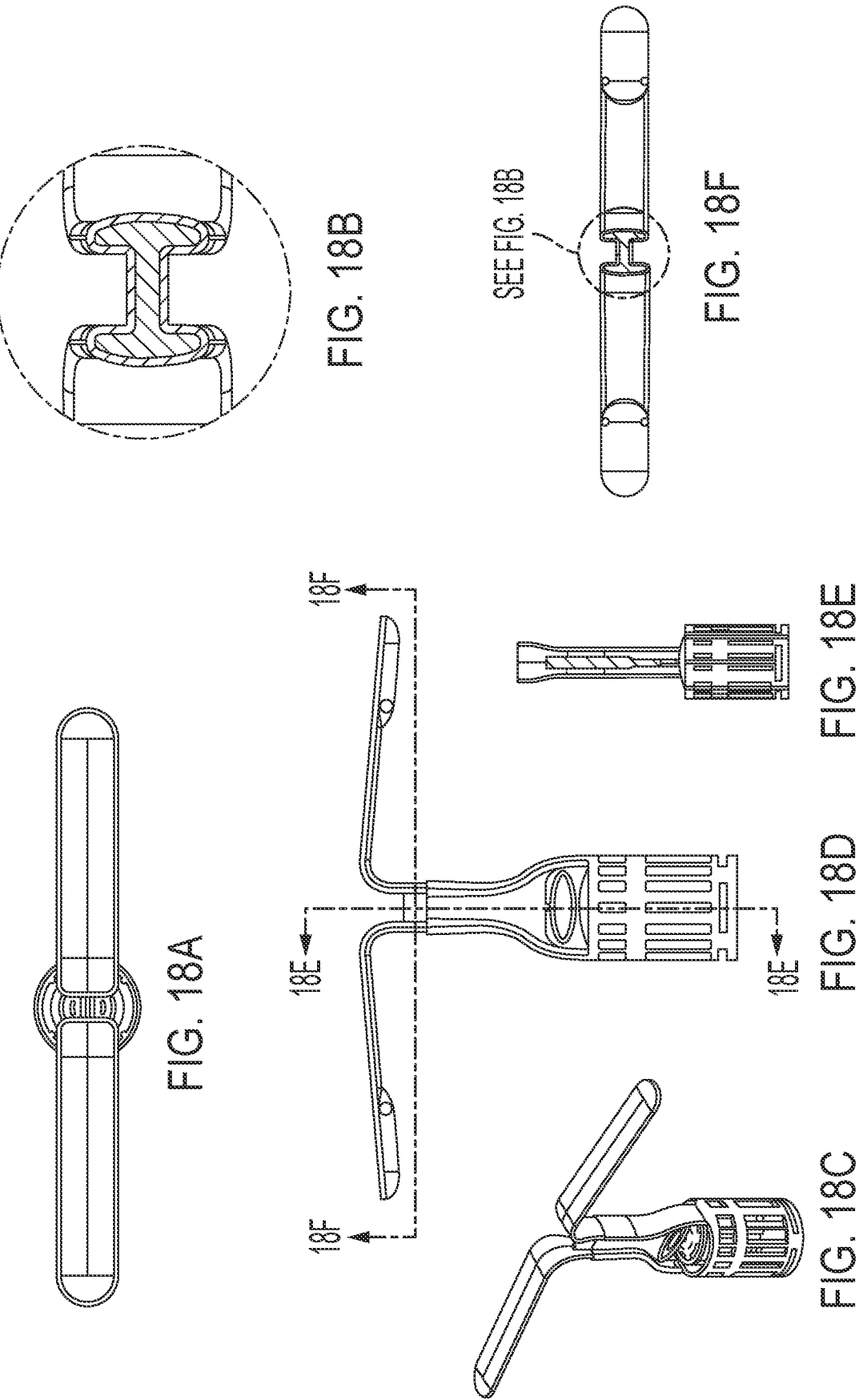

Having thus described the disclosure in general terms, reference will now be made to the accompanying drawings, which are not necessarily drawn to scale, and wherein:

FIG. 1A schematically illustrates a medicament delivery system according to an example aspect of the present disclosure;

FIG. 1B schematically illustrates an osmotic delivery device usable in a medicament delivery system according to various aspects of the present disclosure;

FIGS. 2A, 2B, and 2C schematically illustrate a perspective view, a top view, and a side view, respectively, of the medicament delivery system according to the example aspect shown in FIG. 1A;

FIGS. 3A, 3B, and 3C schematically illustrate a perspective view, a top view, and a side view, respectively, of a medicament delivery system having a different housing removal arrangement, according to another example aspect of the present disclosure;

FIGS. 4A, 4B, and 4C schematically illustrate a perspective view, a top view, and a side view, respectively, of a medicament delivery system having another different housing removal arrangement, according to a further example aspect of the present disclosure;

FIGS. 5A and 5B schematically illustrate perspective views of a medicament delivery system having different retention arrangements, according to other example aspects of the present disclosure;

FIGS. 6A, 6B, and 6C schematically illustrate an example alternate aspect of a medicament delivery system, according to the present disclosure, having a housing with two interlocking portions and cantilevered serpentine retention members;

FIGS. 7A, 7B, 7C, and 7D schematically illustrate an example alternate aspect of a medicament delivery system, according to the present disclosure, having a housing with two interlocking portions and cantilevered serpentine retention members;

FIGS. 8A, 8B, 8C, and 8D schematically illustrate an example alternate aspect of a medicament delivery system, according to the present disclosure, having a housing with two interlocking portions and cantilevered serpentine retention members;

FIGS. 9A, 9B, and 9C schematically illustrate an example alternate aspect of a medicament delivery system, according to the present disclosure, having a housing with two interlocking portions and retention members including elliptical rings;

FIGS. 10A, 10B, 10C, and 10D schematically illustrate an example alternate aspect of a medicament delivery system, according to the present disclosure, having a housing with two interlocking portions and retention members including elliptical rings;

FIGS. 11A, 11B, 11C, and 11D schematically illustrate an example alternate aspect of a medicament delivery system, according to the present disclosure, having a housing with two interlocking portions and retention members including elliptical rings;

FIGS. 12A, 12B, 12C, and 12D schematically illustrate an elongate handle having a hook member engaged with a distal end thereof for engaging a housing removal arrangement of a medicament delivery system, according to one aspect of the present disclosure, for removing the housing from a bodily orifice;

FIGS. 13A, 13B, 13C, 13D, 13E, 13F, and 13G schematically illustrate a removable end cap of a housing of a medicament delivery system, according to one aspect of the present disclosure;

FIG. 13H schematically illustrates a removable end cap of a housing of a medicament delivery system, according to one aspect of the present disclosure, having an elongate tether engaged therewith as a portion of the housing removal arrangement for removing the medicament delivery system from a bodily orifice;

FIGS. 14A, 14B, 14C, 14D, and 14E schematically illustrate an alternate removable end cap of a housing of a medicament delivery system, according to one aspect of the present disclosure;

FIGS. 15A, 15B, 15C, 15D, and 15E schematically illustrate a medicament delivery system, according to one aspect of the present disclosure, having a retention arrangement including opposed retention members extending from a distal end of a stem extending from the housing;

FIGS. 16A, 16B, 16C, 16D, 16E and 16F schematically illustrate a medicament delivery system, according to one aspect of the present disclosure, having a retention arrangement including opposed retention members extending from a distal end of a stem extending from the housing;

FIGS. 17A, 17B, 17C, 17D, and 17E schematically illustrate a medicament delivery system, according to an alternate aspect of the present disclosure, having a retention arrangement including opposed retention members extending from a distal end of a stem extending from the housing; and FIGS. 18A, 18B, 18C, 18D, 18E, and 18F schematically illustrate a medicament delivery system, according to an alternate aspect of the present disclosure, having a retention arrangement including opposed retention members extending from a distal end of a stem extending from the housing.

DETAILED DESCRIPTION

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

FIG. 1A schematically illustrates an intra-orifice medicament delivery system, generally indicated by the numeral 100, according to one aspect of the present disclosure. In such aspects, the system 100 includes a housing 110 having a chamber wall 112 defining an inner chamber 113 therein, extending along a longitudinal axis D from a first end 115 to a second end 116. The chamber wall 112 further defining one or more openings 114 extending from the chamber 113 through the chamber wall 112. In particular aspects, an osmotic delivery device 120 (see, also, FIG. 1B) is disposed within the chamber 113 and includes an osmogen portion 122 and a medicament-including portion 124 disposed within a semipermeable membrane 125.

A retention arrangement 135 is engaged with and extends from the housing 110, either directly or indirectly. In the aspect shown in FIG. 1A, an elongate stem 126 extends from the first end 115 of the housing 110 along the longitudinal axis D, and the retention arrangement 135 comprises one or more retention members 140 extending from the stem 126. In some aspects, each retention member 140 includes a body 141 having a proximate end engaged with the stem 126, and extending to a distal end. In some instances, a termination member 142 is engaged with the distal end of the body 141.

In one example embodiment, the system 100, including the housing 110 and the retention arrangement 135, is particularly adapted to be inserted into a bodily orifice of an animal (e.g., a female mammal such as a pig), the bodily orifice (e.g., a vaginal orifice) being defined by an orifice wall. Upon insertion into the orifice, the system 100 is arranged to deliver a medicament (e.g., from the medicament-including portion 124 of the osmotic delivery device 120) from the chamber 113, through the opening 114, and into the bodily orifice such that the medicament is absorbed into the body of the animal through the orifice wall. As such, in particular aspects of the present disclosure, the system 100 is further arranged such that the retention arrangement 135 is adapted to removably retain the housing 110 within the orifice defined by the orifice wall.

In order to facilitate removability of the system 100 from the orifice, some aspects of the present disclosure further include a housing removal arrangement 150 engaged with the housing 110 or with the retention arrangement 135, wherein the housing removal arrangement 150 is adapted to facilitate removal of the housing 110 from the orifice. In the example aspect shown in FIG. 1A, the housing removal arrangement 150 is engaged with the housing 110 via the stem 126. That is, the housing removal arrangement 150 is engaged with a distal end of the stem 126, opposite to the engagement of the proximal end of the stem 126 with the first end 115 of the housing 110. The retention arrangement 135 can be serially engaged between the housing removal arrangement 150 and the housing 110 or, as shown in FIG. 1A, the retention arrangement 135 is engaged with the stem 126 between the housing removal arrangement 150 and the housing 110. In the particular aspect shown in FIG. 1A, the housing removal arrangement 150 includes a ring member 155.

In some aspects, the system 100 can be arranged such that, when inserted into the bodily orifice, the housing 110 and the retention arrangement 135 are disposed within the orifice, while the housing removal arrangement 150 is disposed outside the orifice. However, in other instances, the housing removal arrangement 150 can also be disposed within the orifice upon insertion of the system 100. In some instances, instead of the directly engaging the housing removal arrangement 150 to remove the system 100 from the orifice (e.g., following delivery of a sufficient dose of the medicament into the orifice), the housing removal arrangement 150 can further include a removal member (see, e.g., element 660 in FIG. 6, element 960 in FIG. 9, or element 1260 in FIG. 12). More particularly, the removal member can include an elongate handle having a distal end including a hook member arranged to engage the ring member 155 for facilitating removal of the housing 110 from the orifice.

As shown in the aspects of FIG. 1A, the retention arrangement 135 includes one or more retention members 140 (e.g. the body 141 thereof) engaged with and extending away from the housing 110 or the stem 126, such that the one or more retention members 140 is arranged to be biased toward and into engagement with the orifice wall for retaining the housing 110 within the orifice. For example, the one or more retention members 140 can be arranged in a cantilevered arrangement in relation to the housing 110 or the stem 126. In such an arrangement, the one or more retention members 140 is flexible, or the engagement between the one or more retention members 140 and the housing 110 or the stem 126 is flexible. As such, the flexibility associated with the one or more retention members 140 causes at least the distal end(s) of the one or more retention members 140 to be biased into interaction with the orifice wall for retaining the housing within the bodily orifice. In some aspects, the housing 110 defines a maximum diameter perpendicular to the longitudinal axis D, and distal end(s) of the one or more retention members 140 or a rounded member (e.g. termination member 142) engaged therewith extends outwardly from the housing 110 or the stem 126 for greater than the maximum diameter of the housing 110. The greater extension of the one or more retention members 140 outside the diameter of the housing 110 facilitates and ensures engagement between the distal end(s) of the one or more retention members 140 and the orifice wall.

This same flexibility associated with the one or more retention members 140 further facilitates and allows the distal end(s) of the one or more retention members 140 to be disengaged from the orifice wall (e.g., in response to a longitudinally outward force applied to the housing removal arrangement 150) for removing the housing 110 from the bodily orifice. That is, in response to the longitudinally outward force applied to the housing removal arrangement 150, the flexible one or more retention members 140 are urged toward the housing 110/stem 126, which allows the housing 110 to be removed through the bodily orifice. In some aspects, in order to facilitate removal of the housing 110 from the bodily orifice and/or prevent perforation of the orifice wall by the distal end(s) of the one or more retention members 140, distal end(s) of the one or more retention members 140 is rounded or includes a rounded member (e.g., termination member 142) engaged therewith.

As further shown in FIG. 1B, the osmogen portion 122 is disposed in contact with the medicament-including portion 124, wherein the semipermeable membrane 125 comprises a coating applied about the osmogen portion 122 and the medicament-including portion 124, collectively. That is, there is not a portion of the membrane 125 or a different membrane between the osmogen portion 122 and the medicament-including portion 124, though such a portion of the membrane or the different membrane can be included between the osmogen portion 122 and the medicament-including portion 124 as necessary or desired. In any instance, the osmogen portion 122 of the osmotic delivery device 120 is arranged to expand and to apply pressure to the medicament-including portion 124 in response to absorption by the osmogen portion 122 of a liquid from within the bodily orifice entering the housing 110 through the one or more openings 114 and permeating through the membrane 125. The medicament-including portion 124 is further arranged to emit a medicament in response to the pressure applied thereto by the expanded osmogen portion 122. That is, the osmotic delivery device 120 is arranged to function, for example, as a pump for emitting the medicament into the chamber 113 and out of the housing 110 into the bodily orifice. Once emitted by the medicament-including portion 124, the medicament exits the housing 110 through the one or more openings 114 such that the medicament is delivered into the bodily orifice.

To facilitate the transport of the liquid from the orifice, or the medicament from the medicament-including portion 124, across the membrane 125, the membrane 125 may be comprised of a semipermeable material, such as a coating composition comprising, for example, cellulose acetate (CA), cellulose acetate butyrate (CAB), and polyethylene glycol (PEG). According to some aspects, the semipermeable material is chosen to allow influx of a bodily fluid (e.g., water), while preventing or limiting efflux of the medicament. Accordingly, in some aspects, one or more membrane orifices 127 (FIG. 1B) may be formed in the membrane 125 (e.g., by drilling) about the medicament-including portion 124 so as to facilitate release of the medicament through the membrane 125. In particular aspects, such formed membrane orifices 127 in the membrane 125 are formed in longitudinal end of the membrane 125 extending over the medicament-releasing portion 124. Accordingly, the emission of the medicament from the osmotic delivery device 120 occurs through the physically-formed holes in the membrane 125 instead of via a permeation mechanism through the intact membrane 125.

In some aspects, the membrane 125, the medicament-including portion 124, and/or the osmogen portion 122 is arranged to cause the medicament-including portion 124 to emit the medicament at a predetermined rate. For example, the osmogen portion 122 can be comprised of, for example, magnesium stearate, which absorbs liquid at a known or controllable rate. In another example, the medicament-including portion 124 includes a medicament comprising, for example, a steroid, a hormone, a cytokine signaling molecule, a pain management drug, a vaccine antigen, an eicosanoid, an immunomodulating agent, a protein, a peptide, a glycoprotein, or combinations thereof associate with or absorbed within a carrier matrix, wherein pressure applied to the carrier matrix causes the medicament to be emitted at a predetermined or controllable rate.

In some aspects, the chamber wall 112 is substantially cylindrical and has opposing first and second ends 115, 116, wherein the housing 110 includes an end wall engaged with each opposing end (see, e.g., elements 1360 and 1402 in FIGS. 13A, 13H, and 14). In such instances, one or both of the end walls 1360, 1402 defines one or more openings (see, e.g., element 1361 in FIG. 13A or 13H). In some such aspects, the medicament-including portion 124 of the osmotic delivery device 120 is disposed adjacent to the one of the end walls 1360, 1402 defining the one or more openings 1361 (or see, e.g., element 114 in FIG. 1A) such that at least a portion of the medicament can be released from the housing 110 through the one or more openings 114, 1361. In yet other aspects, the housing 110 comprises two interlocking portions such as, for example, a body portion 1101 and a cap portion 1102 as shown in FIG. 1A, that cooperate to define the chamber 113 for containing the osmotic delivery device 120 upon engagement therebetween. That is, the end caps 1360, 1402 engaged with the chamber wall 112, or the body portion 1101 engaged with the cap portion 1102 facilitates insertion of the osmotic delivery device 120 into the chamber 113. Moreover, the external shape, contour, or outward configuration of at least the housing 110 is rounded (e.g., no sharp edges or corners) so as to facilitate insertion/removal of the housing 110 (and/or end caps and/or first and second interlocking portions) with respect to the orifice and/or to prevent or reduce the risk of perforation or other damage to the orifice wall.

In some aspects, the osmotic delivery device 120 is cylindrical in correspondence with the chamber 113, which is also cylindrical. In such aspects, the chamber wall 112 can include, for example, one or more protrusions (see, e.g., element 775 in FIG. 7) extending into the chamber 113 from the chamber wall 112. Accordingly, the osmotic delivery device 120 received in the chamber 113 is supported by the one or more protrusions 775 away from the chamber wall 112. In this manner, fluid/liquid from the orifice entering the chamber 113 through the openings 114 is more evenly distributed around the osmotic delivery device 120, for example, to allow the osmogen portion 122 to more evenly and uniformly absorb the fluid/liquid for providing the disclosed pumping function or pressure on the medicament-including portion 124 for emitting the medicament. Further, in additional aspects, the openings 114 defined by the housing 110 may be angled (e.g., a larger opening on the outer surface of the chamber wall 112 tapering to a smaller opening on the inner surface of the chamber wall 112—see, e.g., element 175 in FIGS. 2A-C, 3A-C, 4A-C, and 5A-B), shaped (e.g., as a venturi) or otherwise configured (e.g., as a one-way valve) to draw or provide increased draw of the fluid/liquid from the orifice into the chamber 113.

In yet another aspect, as shown for example in FIG. 1A, the osmogen portion 122 of the osmotic delivery system 120 is disposed toward the first end 115 of the housing 110, while the medicament-including portion 124 is disposed toward the second end 116. In such instances, the second end 116 also includes one or more holes (e.g., element 114 in FIG. 1A), while the one or more membrane orifices 127 formed in the membrane 125 (e.g., by drilling) about the medicament-including portion 124 of the osmotic delivery device 120 are in correspondence therewith. In such an aspect, the medicament released through the membrane orifices 127 in the membrane 125 about a longitudinal end of the medicament-including portion 124 is intended for release from the housing through the one or more holes in the second end 116 of the housing 110. However, if the medicament-including portion 124 is not securely engaged with the chamber wall 112 about the second end 116 of the housing 110, the medicament emitted by the medicament-including portion 124 may tend to travel within the chamber 113, between the chamber wall 112 and about the osmotic delivery device 120 toward the osmogen portion 122. Accordingly, in some aspects, the medicament-including portion 124 may be configured to fit in close tolerance with the chamber wall 112 toward the second end 116, or a biasing member (not shown) may be arranged to bias the osmotic delivery device 120 toward the end wall of the chamber 113 toward the second end 116 such that the membrane 125 engages the end wall of the chamber 113. In such instances, the emitted medicament is urged to pass through the openings 114 and out of the chamber 113, and not remain within the chamber 113.

According to some aspects of the present disclosure, an erodible object may be used in place of, or in combination with, the osmotic delivery device 120. In some instances, the erodible object may be in the form of a tablet. The erodible object may include a medicament component capable of releasing a pharmaceutically active ingredient at a predictable release rate, such as, for example, for at least seven days. The erodible object may be either a physical blend or a chemical mix of active ingredients with slowly dissolving (erodible) or swellable polymers and other inactive ingredients. The release rate of the active ingredient from the erodible object may be a function of each ingredient's composition and their physicochemical characteristics. In general, release rate control from the erodible object may be achieved by controlling fluid (e.g., water) influx into the retention arrangement 135. Dissolution rate control may or may not be combined with solubility enhancement techniques to achieve the desired rate or duration of medicament release. In some instances, the erodible object may include one or more active ingredients plus excipients, and would have disintegrated/dissolved (erodible) at the time of the complete release of a medicament payload, thereby making the retention arrangement 135 re-useable or easy to dispose. The medicament component may include a medicament comprising, for example, a steroid, a hormone, a cytokine signaling molecule, a pain management drug, a vaccine antigen, an eicosanoid, an immunomodulating agent, a protein, a peptide, a glycoprotein, or combinations thereof. The medicament component may be associated with or absorbed within a carrier matrix.

In various aspects, the system 100, including the housing 110, the stem 126, the one or more retention members 140, and the housing removal arrangement 150, is comprised of a polymeric material such as, for example, Nylon 6/6, and formed, for example, in an injection molding process. However, one of ordinary skill in the art will appreciate that the system 100 may be comprised of many different materials, whether polymeric or non-polymeric, or combinations thereof, as necessary or desired.

FIGS. 1A and 2A-C schematically illustrate embodiments wherein the termination members 142 of the retention members 140 are rings engaged with the distal ends of the body 141. The housing removal arrangement 150 is also engaged with a distal end of the stem 126 and comprises a ring member 155. In addition, the housing 110 is configured to include an interlocking body portion 1101 and cap portion 1102.

FIGS. 3A-C schematically illustrate an embodiment of a medicament delivery system 300, similar to the embodiment shown in FIGS. 1A and 2A-2C, which includes a housing removal arrangement 150 configured to include a textured gripping portion 350 for facilitating gripping by a user for insertion/removal of the system 300 with respect to the orifice.

FIGS. 4A-C schematically illustrate an embodiment of a medicament delivery system 400 similar to the embodiment shown in FIGS. 3A-3C, wherein the textured gripping portion 450 of the housing removal arrangement 150 is tapered and reduced in size.

FIGS. 5A-B schematically illustrate two embodiments of a medicament delivery system 500A, 500B similar to the embodiment shown in FIGS. 1A and 2A-2C, a reduced section gripping portion 550 of the ring member 155 of the housing removal arrangement 150. In addition, the termination member of the retention members can be a spherical termination member 542A (FIG. 5A) as opposed to a ring member 542B (FIG. 5B).

FIG. 6 schematically illustrates an embodiment of a medicament delivery system 600 including a body portion 6101 and interlocking cap portion 6102, similar to the embodiment shown in FIGS. 1A and 2A-2C. In addition, resilient retention members 640 include a serpentine body 641 extending from a stem 626 to a distal end, wherein the distal end has a rounded (arcuate or convex) termination member 642 engaged therewith. The serpentine body 641 in addition to the flexibility of the material comprising the serpentine body 641 provides resiliency or a biasing force urging the rounded termination member into engagement with the orifice wall. In addition, a removal member 660 includes an elongate handle having a distal end having a hook member arranged to engage the ring member 655 for facilitating removal of the housing 610 from the orifice. The dimensions indicated in FIG. 6 are illustrative only, and non-limiting.

FIGS. 7 and 8 schematically illustrate alternate embodiments of a medicament delivery system 700, 800, similar to the embodiment shown in FIG. 6, wherein the rounded termination members 742, 842 include an overmolded outer layer 7401, 8401. A reduced section gripping portion 750, 850 of the ring member 755, 855 of the housing removal arrangement 750, 850 is also shown. The dimensions indicated in FIGS. 7 and 8 are illustrative only, and non-limiting.

FIGS. 9-11 schematically illustrate alternate embodiments of a medicament delivery system 900, 1000, 1100, similar to the embodiments shown in FIGS. 6-8, wherein the body 941, 1041, 1141 of the resilient retention members 940, 1040, 1140 are configured as an elliptical ring. One skilled in art will appreciate, however, that the elliptical ring could be replaced by a circular ring, if necessary or desired. The elliptical ring body 941, 1041, 1141 in addition to the flexibility of the material comprising the elliptical ring body 941, 1041, 1141 provides resiliency or a biasing force urging the rounded termination member into engagement with the orifice wall. In addition, a removal member 960 in FIG. 9 includes an elongate handle having a distal end having a hook member arranged to engage the ring member for facilitating removal of the housing from the orifice. The dimensions indicated in FIGS. 9-11 are illustrative only, and non-limiting.

FIG. 12 schematically illustrates an embodiment of a removal member 1260, similar to those shown in FIGS. 6 and 9, including an elongate handle having a distal end having a hook member arranged to engage the ring member of a housing removal arrangement of a medicament delivery system, for facilitating removal of the housing from the orifice. The dimensions indicated in FIG. 12 are illustrative only, and non-limiting.

FIGS. 13A-H and 14 schematically illustrate end cap portions 1360, 1402 of medicament delivery system that implements a cylindrical chamber wall configured to interlockingly receive the illustrated end cap portions 1360, 1402. The dimensions indicated in FIGS. 13A and 14 are illustrative only, and non-limiting. In the aspects shown in FIGS. 13A-H, the end cap portion 1360 defines an opening 1361 through which the medicament emitted by the osmotic delivery device is dispensed. In some instances, the end cap portion may define a further opening 1362 to receive and engage a removal member 1363 (see, e.g., FIG. 13H) configured to facilitate removal of the medicament delivery system from the orifice.

FIGS. 15-18 schematically illustrate alternate embodiments of a medicament delivery system according to further aspects of the disclosure wherein, in such aspects, laterally outward-extending retention members form a "T" shape configuration of the retention arrangement. In this manner, the retention arrangement is configured to engage the housing having either or both of the end cap portions illustrated in FIG. 13A, 13H, or 14. In such aspects, the end cap portion 1360 having the removal member 1363 (see, e.g., FIG. 13H) is engaged with one longitudinal end of the housing, while the retention members/retention arrangement are engaged with the opposite longitudinal end of the housing. Configured in this manner, the retention arrangement is disposed opposite the housing from the housing removal arrangement, and the retention arrangement thus leads the housing upon insertion into the orifice along the longitudinal axis D.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "I" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

What is claimed is:

1. An intra-orifice medicament delivery system, comprising:

a housing having a chamber wall defining an inner chamber extending along a longitudinal axis, the chamber wall further defining one or more openings extending from the chamber through the chamber wall;

a retention arrangement engaged with and extending from the housing, the retention arrangement being adapted to removably retain the housing within a bodily orifice defined by an orifice wall;

an osmotic delivery device disposed within the chamber and including an osmogen portion and a medicament-including portion, both portions being disposed within a semipermeable membrane, the osmogen portion being arranged to expand and to apply pressure to the medicament-including portion in response to absorption of a liquid from within the orifice permeating through the semipermeable membrane, the medicament-including portion being arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice; and a housing removal arrangement engaged with the housing or the retention arrangement, the housing removal arrangement being adapted to facilitate removal of the housing from the bodily orifice, and wherein the housing removal arrangement is engaged with the housing via a stem arranged therebetween, the stem extending along the longitudinal axis.

2. The system of claim 1, wherein the housing removal arrangement includes a ring member.

3. The system of claim 2, wherein the housing removal arrangement further includes an elongate handle having a distal end including a hook member arranged to engage the ring member for facilitating removal of the housing from the bodily orifice.

4. The system of claim 1, wherein the retention arrangement is engaged with a first end of the housing and the housing removal arrangement is engaged with a second end of the housing.

5. The system of claim 1, wherein the retention arrangement is engaged with the stem between the housing removal arrangement and the housing.

6. The system of claim 1, wherein the retention arrangement includes one or more retention members engaged with and extending away from the housing or the stem, such that the one or more retention members is arranged to be biased toward and into engagement with the orifice wall for retaining the housing within the bodily orifice.

7. The system of claim 6, wherein the one or more retention members is arranged in a cantilevered arrangement in relation to the housing or the stem.

8. The system of claim 6, wherein the one or more retention members is flexible or wherein the engagement between the one or more retention members and the housing or the stem is flexible, the flexibility associated with the one or more retention members biasing the one or more retention members into interaction with the orifice wall for retaining the housing within the bodily orifice, or facilitating disengagement of the one or more retention members from the orifice wall for removing the housing from the bodily orifice.

9. The system of claim 6, wherein a distal end of the one or more retention members is rounded or includes a rounded member engaged therewith so as to prevent perforation of the orifice wall by the distal ends or to facilitate removal of the housing from the bodily orifice.

10. The system of claim 9, wherein the housing defines a maximum diameter perpendicular to the longitudinal axis, and wherein the distal end of the one or more retention members or the rounded member engaged therewith extends outwardly from the stem for greater than the maximum diameter of the housing.

11. The system of claim 1, wherein the membrane, the medicament-including portion, or the osmogen portion is arranged to cause the medicament-including portion to emit the medicament at a predetermined rate.

12. The system of claim 1, wherein the one or more openings defined by the chamber wall and extending from the chamber through the chamber wall define a relatively larger open area about an outer surface of the chamber wall and a relatively smaller open area about an inner surface of the chamber wall so as to funnel liquid from the orifice into the chamber.

13. The system of claim 1, wherein the osmogen portion is disposed in contact with the medicament-including portion, and wherein the semipermeable membrane comprises a coating applied about the osmogen portion and the medicament-including portion.

14. The system of claim 1, wherein the housing comprises two interlocking portions containing the osmotic delivery device within the chamber defined thereby upon engagement therebetween.

15. An intra-orifice medicament delivery system, comprising:
  a housing having a chamber wall defining an inner chamber extending along a longitudinal axis, the chamber wall further defining one or more openings extending from the chamber through the chamber wall;

a retention arrangement engaged with and extending from the housing, the retention arrangement being adapted to removably retain the housing within a bodily orifice defined by an orifice wall;
  an osmotic delivery device disposed within the chamber and including an osmogen portion and a medicament-including portion, both portions being disposed within a semipermeable membrane, the osmogen portion being arranged to expand and to apply pressure to the medicament-including portion in response to absorption of a liquid from within the orifice permeating through the semipermeable membrane, the medicament-including portion being arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice; and
  a housing removal arrangement engaged with the housing or the retention arrangement, the housing removal arrangement being adapted to facilitate removal of the housing from the bodily orifice, and wherein the retention arrangement is serially engaged between the housing removal arrangement and the housing.

16. An intra-orifice medicament delivery system, comprising:
  a housing having a chamber wall defining an inner chamber extending along a longitudinal axis, the chamber wall further defining one or more openings extending from the chamber through the chamber wall;
  a retention arrangement engaged with and extending from the housing, the retention arrangement being adapted to removably retain the housing within a bodily orifice defined by an orifice wall;
  an osmotic delivery device disposed within the chamber and including an osmogen portion and a medicament-including portion, both portions being disposed within a semipermeable membrane, the osmogen portion being arranged to expand and to apply pressure to the medicament-including portion in response to absorption of a liquid from within the orifice permeating through the semipermeable membrane, the medicament-including portion being arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice;
  a housing removal arrangement engaged with the housing or the retention arrangement, the housing removal arrangement being adapted to facilitate removal of the housing from the bodily orifice; and
  one or more protrusions extending from the chamber wall into the chamber, the one or more protrusions facilitating spacing of the osmotic delivery device away from the chamber wall to facilitate circulation of liquid about the osmotic delivery device.

17. An intra-orifice medicament delivery system, comprising:
  a housing having a chamber wall defining an inner chamber extending along a longitudinal axis, the chamber wall further defining one or more openings extending from the chamber through the chamber wall;

a retention arrangement engaged with and extending from the housing, the retention arrangement being adapted to removably retain the housing within a bodily orifice defined by an orifice wall;

an osmotic delivery device disposed within the chamber and including an osmogen portion and a medicament-including portion, both portions being disposed within a semipermeable membrane, the osmogen portion being arranged to expand and to apply pressure to the medicament-including portion in response to absorption of a liquid from within the orifice permeating through the semipermeable membrane, the medicament-including portion being arranged to emit a medicament in response to the pressure applied by the expanded osmogen portion, with the medicament exiting through a membrane orifice defined by the semipermeable membrane and subsequently exiting the housing through the one or more openings such that the medicament is delivered into the bodily orifice;

a housing removal arrangement engaged with the housing or the retention arrangement, the housing removal arrangement being adapted to facilitate removal of the housing from the bodily orifice; and wherein the chamber wall is substantially cylindrical and has opposing first and second ends, wherein the housing includes first and second end walls, the first end wall engaged with the first end while the second end wall is engaged with the second end, and wherein the second end wall defines one or more openings.

18. The system of claim 17, wherein the medicament-including portion of the osmotic delivery device is disposed adjacent to the second end wall defining the one or more openings.

19. The system of claim 18, comprising a biasing arrangement engaged between the chamber wall and the osmotic delivery device, the biasing arrangement being arranged to bias the osmotic delivery device against the second end wall so as to facilitate emission of the medicament from the medicament-including portion through the one or more openings defined by the second end wall.

20. A method of forming an intra-orifice medicament delivery system, comprising:

forming a housing having a chamber wall defining an inner chamber extending along a longitudinal axis, such that the chamber wall defines one or more openings extending from the chamber through the chamber wall;

engaging a retention arrangement with the housing such that the retention arrangement extends from the housing and is adapted to removably retain the housing within a bodily orifice defined by an orifice wall;

disposing an osmotic delivery device, including an osmogen portion and a medicament-including portion where both portions are disposed within a semipermeable membrane, within the chamber, such that the osmogen portion is arranged to expand and to apply pressure to the medicament-including portion in response to absorption of a liquid from within the orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice; and engaging a housing removal arrangement with the housing or the retention arrangement, wherein the housing removal arrangement is adapted to facilitate removal of the housing from the bodily orifice, and further wherein the housing removal arrangement is engaged with the housing via a stem arranged therebetween and extending along the longitudinal axis.

21. The method of claim 20, wherein engaging the housing removal arrangement comprises engaging a ring member of the housing removal arrangement with the housing or the retention arrangement.

22. The method of claim 21, comprising engaging the ring member of the housing removal arrangement with a distal end of an elongate handle, the distal end including a hook member arranged to engage the ring member for facilitating removal of the housing from the bodily orifice.

23. The method of claim 20, wherein engaging the retention arrangement comprises serially engaging the retention arrangement between the housing removal arrangement and the housing.

24. The method of claim 20, comprising arranging the semipermeable membrane, the medicament-including portion, or the osmogen portion to cause the medicament-including portion to emit the medicament at a predetermined rate.

25. The method of claim 20, comprising forming the one or more openings defined by the chamber wall such that the one or more openings define a relatively larger open area about an outer surface of the chamber wall and a relatively smaller open area about an inner surface of the chamber wall.

26. The method of claim 20, wherein disposing the osmotic delivery device comprises disposing the osmotic delivery device within a first portion of the housing and engaging a second portion of the housing with the first portion such that the two portions interlock to contain the osmotic delivery device within the chamber defined thereby upon engagement therebetween.

27. A method of forming an intra-orifice medicament delivery system, comprising:

forming a housing having a chamber wall defining an inner chamber extending along a longitudinal axis, such that the chamber wall defines one or more openings extending from the chamber through the chamber wall;

engaging a retention arrangement with the housing such that the retention arrangement extends from the housing and is adapted to removably retain the housing within a bodily orifice defined by an orifice wall;

disposing an osmotic delivery device, including an osmogen portion and a medicament-including portion where both portions are disposed within a semipermeable membrane, within the chamber, such that the osmogen portion is arranged to expand and to apply pressure to the medicament-including portion in response to absorption of a liquid from within the orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice; and engaging a housing removal arrangement with the housing or the retention arrangement, wherein the housing removal arrangement is adapted to facilitate removal of the housing from the bodily orifice, and further wherein the housing removal arrangement is engaged with the housing via a stem arranged therebetween and extending along the longitudinal axis, wherein engaging the retention arrangement comprises engaging the retention arrangement with the stem between the housing removal arrangement and the housing.

28. A method of forming an intra-orifice medicament delivery system, comprising:

forming a housing having a chamber wall defining an inner chamber extending along a longitudinal axis, such that the chamber wall defines one or more openings extending from the chamber through the chamber wall;

engaging a retention arrangement with the housing such that the retention arrangement extends from the housing and is adapted to removably retain the housing within a bodily orifice defined by an orifice wall;

disposing an osmotic delivery device, including an osmogen portion and a medicament-including portion where both portions are disposed within a semipermeable membrane, within the chamber, such that the osmogen portion is arranged to expand and to apply pressure to the medicament-including portion in response to absorption of a liquid from within the orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice; and engaging a housing removal arrangement with the housing or the retention arrangement, wherein the housing removal arrangement is adapted to facilitate removal of the housing from the bodily orifice, and further wherein the housing removal arrangement is engaged with the housing via a stem arranged therebetween and extending along the longitudinal axis, wherein engaging the retention arrangement comprises engaging one or more retention members with and to extend away from the housing or the stem, such that the one or more retention members is arranged to be biased toward and into engagement with the orifice wall for retaining the housing within the bodily orifice.

29. The method of claim 28, comprising arranging the one or more retention members in a cantilevered arrangement in relation to the housing or the stem.

30. The method of claim 28, comprising rounding a distal end of at least one of the one or more retention members or engaging a rounded member with each distal end so as to prevent perforation of the orifice wall by the distal ends or to facilitate removal of the housing from the bodily orifice.

31. The method of claim 30, wherein the housing defines a maximum diameter perpendicular to the longitudinal axis, and wherein rounding the distal end or engaging the rounded member comprises rounding the distal end or engaging the rounded member with each distal end such that the distal end of the one or more retention members or the rounded member engaged therewith extends outwardly from the stem for greater than the maximum diameter of the housing.

32. A method of forming an intra-orifice medicament delivery system, comprising:

forming a housing having a chamber wall defining an inner chamber extending along a longitudinal axis, such that the chamber wall defines one or more openings extending from the chamber through the chamber wall;

engaging a retention arrangement with the housing such that the retention arrangement extends from the housing and is adapted to removably retain the housing within a bodily orifice defined by an orifice wall;

disposing an osmotic delivery device, including an osmogen portion and a medicament-including portion where both portions are disposed within a semipermeable membrane, within the chamber, such that the osmogen portion is arranged to expand and to apply pressure to the medicament-including portion in response to absorption of a liquid from within the orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice; and forming one or more protrusions extending from the chamber wall into the chamber, the one or more protrusions facilitating spacing of the osmotic delivery device away from the chamber wall to facilitate circulation of liquid about the osmotic delivery device.

33. A method of forming an intra-orifice medicament delivery system, comprising:

forming a housing having a chamber wall defining an inner chamber extending along a longitudinal axis, such that the chamber wall defines one or more openings extending from the chamber through the chamber wall;

engaging a retention arrangement with the housing such that the retention arrangement extends from the housing and is adapted to removably retain the housing within a bodily orifice defined by an orifice wall; and disposing an osmotic delivery device, including an osmogen portion and a medicament-including portion where both portions are disposed within a semipermeable membrane, within the chamber, such that the osmogen portion is arranged to expand and to apply pressure to the medicament-including portion in response to absorption of a liquid from within the orifice permeating through the semipermeable membrane, such that the medicament-including portion is arranged to emit a medicament in response to the pressure applied by the expanded osmogen portion, and such that the medicament exits through a membrane orifice defined by the semipermeable membrane and subsequently exits the housing through the one or more openings and is delivered into the bodily orifice, wherein forming the housing comprises forming the housing such that the chamber wall is substantially cylindrical and has opposing first and second ends, and engaging a first end wall with the first end and engaging a second end wall with the second end, wherein the second end wall defines one or more openings.

34. The method of claim 33, wherein disposing the osmotic delivery device comprises disposing the osmotic delivery device within the chamber such that the medicament-including portion thereof is disposed adjacent to the second end wall defining the one or more openings.

35. The method of claim 34, comprising engaging a biasing arrangement between the chamber wall and the osmotic delivery device, such that the biasing arrangement is arranged to bias the osmotic delivery device against the second end wall so as to facilitate emission of the medicament from the medicament-including portion through the one or more openings defined by the second end wall.

* * * * *